(12) United States Patent
Jiang

(10) Patent No.: US 10,568,913 B2
(45) Date of Patent: Feb. 25, 2020

(54) METHOD FOR GENERATING MATURE β-LIKE CELLS

(71) Applicant: The University of Western Australia, Nedlands, Western Australia (AU)

(72) Inventor: Fang-Xu Jiang, Nedlands (AU)

(73) Assignee: Healthregen PTY LTD, Scarborough, West Australia (AU)

(*) Notice: Subject to any disclaimer, the term of this patent is extended or adjusted under 35 U.S.C. 154(b) by 0 days.

(21) Appl. No.: 14/780,445

(22) PCT Filed: Mar. 28, 2014

(86) PCT No.: PCT/AU2014/000342
§ 371 (c)(1),
(2) Date: Sep. 25, 2015

(87) PCT Pub. No.: WO2014/153620
PCT Pub. Date: Oct. 2, 2014

(65) Prior Publication Data
US 2016/0045554 A1    Feb. 18, 2016

(30) Foreign Application Priority Data

Mar. 28, 2013   (AU) ................. 2013901098

(51) Int. Cl.
*A61K 35/39*    (2015.01)
*C12N 5/071*    (2010.01)

(52) U.S. Cl.
CPC ............ *A61K 35/39* (2013.01); *C12N 5/0676* (2013.01); *C12N 2501/40* (2013.01); *C12N 2506/22* (2013.01)

(58) Field of Classification Search
CPC ............. C12N 5/0676; C12N 2500/38; C12N 2506/22; C12N 2501/40; A61K 35/39
(Continued)

(56) References Cited

U.S. PATENT DOCUMENTS

2009/0004152 A1  1/2009  Martinson et al.
2011/0091433 A1  4/2011  Abuljadayel

FOREIGN PATENT DOCUMENTS

WO  2001/060979 A1   8/2001
WO  2006/108361 A1   10/2006
WO  2006/136374 A2   12/2006

OTHER PUBLICATIONS

Saito et al. Generation of Glucose-Responsive Functional Islets with a Three-Dimensional Structure from Mouse Fetal Pancreatic Cells and iPS Cells In Vitro. PLoS One (2011), v6(12), e28209, 7 pages.*

(Continued)

*Primary Examiner* — Sean C. Barron
(74) *Attorney, Agent, or Firm* — Marshall, Gerstein & Borun LLP

(57) ABSTRACT

The present invention relates to methods for generating mature insulin-producing β-like cells comprising the steps: (a) isolating, purifying and/or enriching β-cell progenitor cells from a population of cells; (b) differentiation of the β-cell progenitor cells into immature insulin-producing β-like cells; and (c) maturation of the immature insulin-producing β-like cells into mature insulin-producing β-like cells, comprising exposing the immature insulin-producing β-like cells to calcitriol or an analogue thereof. More particularly, the present invention relates to methods for generating mature insulin-producing β-like cells for use in treating diabetes.

8 Claims, 27 Drawing Sheets
Specification includes a Sequence Listing.

(58) Field of Classification Search
USPC .................. 424/93.7; 435/34, 377, 6.12, 7.1
See application file for complete search history.

(56) References Cited

OTHER PUBLICATIONS

Bitterman et al. Inhibition of Silencing and Accelerated Aging by Nicotinamide, a Putative Negative Regulator of Yeast Sir2 and Human SIRT1. Journal of Biological Chemistry (2009), v277(47), p. 45099-45107.*

Yang et al. Activation of SIRT1 by Resveratrol Represses Transcription of the Gene for the Cytosolic Form of Phosphoenolpyruvate Carboxykinase (GTP) by Deacetylating Hepatic Nuclear Factor 4-alpha. Journal of Biological Chemistry (2009), v284(40), p. 27042-27053.*

Wu et al. Streptozotocin-Induced Diabetic Models in Mice and Rats. Current Protocols in Immunology (2008), supplement 40, 5.47.1-5.47.14.*

Calcitriol (2008), 5 page reprint from drugs.com.*

A.J.F. King. The use of animal models in diabetes research. British Journal of Pharmacology (2012), v166, p. 877-894.*

Zhang et al. Highly efficient differentiation of human ES cells and iPS cells into mature pancreatic insulin-producing cells. Cell Research (2009), v19, p. 429-438.*

Suzuki et al. 2-Anilinobenzamides as SIRT Inhibitors. ChemMedChem (2006), v1, p. 1059-1062.*

Pubchem CID 936—Nicotinamide. Create date: Sep. 16, 2004. (Year: 2004).*

Pubchem CID 5280453—Calcitriol. Create date: Sep. 16, 2004. (Year: 2004).*

Cheng et al. A novel role for vitamin D: modulation of expression and function of the local renin-angiotensin system in mouse pancreatic islets. Diabetologia (2011), v54, p. 2077-2081. (Year: 2011).*

Clark et al. 1,25-Dihydroxyvitamin D3 target cells in immature pancreatic islets. The American journal of physiology (1987), v253(1), E99-105. (Year: 1987).*

Jiang et al. Generation of Insulin-Producing Islet-Like Clusters from Human Embryonic Stem Cells. Stem Cells (2007), 25, 1940-1953. (Year: 2007).*

Saito et al., "Generation of Glucose-Responsive Functional Islets with a Three-Dimensional Structure from Mouse Fetal Panccreatic Cells and iPS Cells In Vitro", PLoS One, 2011, vol. 6, e28209, pp. 1-7.

Otonkoski et al., "Nicotinamide Is a Potent Inducer of Endocrine Differentiation in Cultured Human Fetal Pancreatic Cells", J. Clin. Invest., 1993, vol. 92, pp. 1459-1466.

Ataie-Jafari et al., "A randomized placebo-controlled trial of alphacalcidol on the preservation of beta cell function in children with recent onset type 1 diabetes", Clin. Nutr., Jan. 2013, vol. 32, pp. 911-917.

Borissova et al., "The Effect of Vitamin D3 on Insulin Secretion and Peripheral Insulin Sensitivity in Type 2 Diabetic Patients", Int. J. Clin. Pract., 2003, vol. 57, pp. 258-261.

* cited by examiner

METHOD FOR GENERATING MATURE β-LIKE CELLS

CROSS-REFERENCE TO RELATED APPLICATIONS

This application is a U.S. National Stage application of PCT/AU2014/000342 filed 28 Mar. 2014, which claims priority to Australian Patent Application No. 2013901098 filed 28 Mar. 2013, the entire disclosures of which are hereby incorporated herein by reference in their entireties.

TECHNICAL FIELD

The present invention relates to methods for generating mature insulin-producing β-like cells. More particularly, the present invention relates to methods for generating mature insulin-producing β-like cells for use in treating diabetes.

BACKGROUND ART

The following discussion of the background art is intended to facilitate an understanding of the present invention only. The discussion is not an acknowledgement or admission that any of the material referred to is or was part of the common general knowledge as at the priority date of the application.

Diabetes mellitus (diabetes) is a chronic metabolic disorder affecting hundreds of millions of people worldwide, where the hormone insulin, is not produced in sufficient amounts or peripheral tissues are not sensitive enough to this hormone to efficiently convert glucose in the blood into energy. Hence, diabetes is caused by an absolute or relative insulin deficiency. The former causes mainly Type 1 diabetes as the result of autoimmune destruction of insulin-producing cells, and the latter causes Type 2 diabetes as a progression of insulin resistance.

Abnormalities of glucose metabolism as a result of insulin deficiency can produce acute, potentially life-threatening metabolic disturbances as well as chronic, vascular complications with significant morbidity and mortality. In addition to its physical and psychological effects, the treatment burden of the disease is considerable, as it requires a major adjustment to everyday activities including diet, exercise, occupation and recreational activities. At present, the only routinely available therapy is exogenously administered insulin given as either multiple daily injections or continuous subcutaneous infusion (pump). The ultimate goal, therefore, would be to cure the disease by generating a renewable source of transplantable human, insulin-secreting β cells in vitro and/or to regenerate endogenous β cells in vivo, should autoimmunity be controlled.

The normal pancreas has about one million islets, and although a person can lose over 80% of these before diabetes develops, transplanting far more than 20% of the total seems to be necessary before blood sugars can be corrected. Laboratories such as Islet Sheet Medical in San Francisco estimate 700,000 islets are needed for total reversal of diabetes.

Differentiation of functional insulin-secreting β cells from a variety of less specialised, stem and/or progenitor cells for use in replacement cell therapy as a cure for Type 1 diabetes has, therefore, been the focus of intensive research over the last decade, aiming for a fundamentally better, long-term way to manage the disease. The development of stem cell or other cell-based treatment of diabetes, known collectively as cellular therapy, has the potential to restore normal glycaemic control in diabetes, and is the most important focus of companies with long-term vision in the field of diabetes management.

The ability to differentiate embryonic stem cells into insulin-secreting cells initially showed great promise, but functional β cells have so far not been produced in vitro. Currently, there are no cellular therapy products present in the market. A recently planned clinical trial for a potential new commercial product has been limited by the fact it requires at least 4 months (even in mice) after transplantation before cell maturity is reached and hyperglycaemia is controlled, and co-administration of insulin is also required.

Some progress has been made with differentiation of insulin-secreting β cells, including demonstration of insulin-producing β cells from culture of heterogeneous cellular populations from various sources, such as adult pancreatic ductal epithelium and acinar tissue. Hyperglycemia could be reversed after transplantation in some studies. Nevertheless, no evidence was provided that these β cells were indeed differentiated from defined animal or human pancreatic/islet progenitors; nor purified populations have been shown to give rise to mature endocrine cells in an in vitro system.

Therefore, replacement cell therapy as a cure for Type 1 diabetes is held back by a major impediment: functional insulin-secreting β cells have not yet been successfully differentiated from defined pancreatic progenitors or any other stem cell and/or progenitor source. This is as a result of a significant lack of knowledge of the signals that regulate late differentiation and maturation of islet cells, a dearth of specific markers for purification of their progenitors, as well as lack of an effective differentiation system within which the differentiation of these progenitors could occur.

It is against this background that the present invention has been developed.

SUMMARY OF INVENTION

The present invention provides a method for generating insulin-producing β-like cells, comprising the steps:
  a) isolating, purifying and/or enriching β-cell progenitor cells from a population of cells;
  b) differentiation of the β-cell progenitor cells into immature insulin-producing β-like cells; and
  c) maturation of the immature insulin-producing β-like cells into mature insulin-producing β-like cells, comprising exposing the immature insulin-producing β-like cells to calcitriol or an analogue thereof.

In one form of the invention, the step of differentiation of the β-cell progenitor cells comprises inhibiting Sirt1 in the β-cell progenitor cells. Preferably, inhibiting Sirt1 in the β-cell progenitor cells comprises exposing the β-cell progenitor cells to a Sirt1 inhibitor. Preferably, the Sirt1 inhibitor is nicotinamide or an analogue thereof.

Accordingly, the inventors have revealed that the method of the invention can produce mature, insulin-producing β-like cells that display features characteristic of functional mature β cells. When transplanted into a subject, these mature insulin-producing β-like cells will aid in the stabilization and amelioration of blood glucose levels, preferably without the requirement of exogenous insulin injections. Therefore, providing long-term benefits to the subject in the management of diabetes from immediate removal of the need for daily injections and the potential deleterious effects of non-compliance.

Cell sorting is the preferred means for isolating, purifying and/or enriching β-cell progenitor cells from a population of cells. Cell sorting may use Flow Activated Cell Sorting (FACS), single cell sorting methodologies (such as IsoRaft array or DEPArray technologies), Magnetic Cell sorting methodologies (such as magnetic activated cell sorting or SEP systems) or any other suitable method known in the field. Desirably, the cell sorting method deployed for cell sorting of the β-cell progenitor cells will use at least one cell surface marker selected from the group comprising: E-cadherin, alpha 6 integrin, CD133, or another critical islet progenitor marker. More preferably, the β-cell progenitor cells express a high level of Neurogenin3 (Ngn3) or another critical islet progenitor marker. In a particularly preferred form of the invention the cells selected are Ngn3$^+$ Islet Progenitors.

In an embodiment of the invention the method of the invention can comprise an additional step of analysing the mature insulin-producing β-like cells in vitro to determine the levels of expression of insulin in response to exposure of the β-like cells to glucose.

In yet another embodiment, the method of the invention can comprise an additional step of transplanting into a subject, insulin-producing β-like cells obtained by the method of the invention. The subject will preferably have diabetes mellitus, and in particular, Type I diabetes mellitus. The subject is preferably a human.

The method of the invention also provides a method for treating a subject with diabetes mellitus, comprising the step of: transplanting into a subject, insulin-producing β-like cells obtained by a method of the invention as herein described.

The invention further provides for the use of insulin-producing β-like cells obtained by a method of the invention as herein described, for the treatment of diabetes mellitus in a subject. The subject is preferably a human.

In a further embodiment of the invention, the invention provides a method of treating a subject with diabetes mellitus comprising one or both of the steps:
 a) inhibiting Sirt1 in β cell progenitors of the subject; and
 b) exposing immature β-like cells of the subject to calcitriol or an analogue thereof.

The one or both steps are preferably performed upon the subject. The one or both steps are preferably performed on the β cells of the subject. The β cells preferably comprise cells that have de-differentiated from mature insulin-producing β cells in the subject, and the one or both steps produce insulin-producing β cells from the de-differentiated β cells or immature β-like cells. The subject preferably has Type 2 diabetes mellitus. More preferably, the subject is a human.

In a third embodiment of the invention, the invention provides a mature insulin-secreting β-like cell obtained by a method of the invention as described herein.

In a fourth embodiment the invention extends to the use of the above methods in the manufacture of a medicament for the treatment of insulin related ailments. More specifically the invention is directed in this embodiment to the use of insulin-producing β cells that have been re-differentiated from de-differentiated β cells or matured from immature β-like cells in the manufacture of a medicament for the treatment of diabetes. Medicaments produced by the above method are preferably capable of use in the treatment of diabetes mellitus (eg. Type 2 diabetes mellitus).

Other aspects and advantages of the invention will become apparent to those skilled in the art from a review of the ensuing description of several non-limiting embodiments thereof.

BRIEF DESCRIPTION OF THE DRAWINGS

This description is included solely for the purposes of exemplifying the present invention. It should not be understood as a restriction on the broad summary, disclosure or description of the invention as set out above. The description will be made with reference to the accompanying drawings in which.

DETAILED DESCRIPTION OF THE INVENTION

Figure 1A:
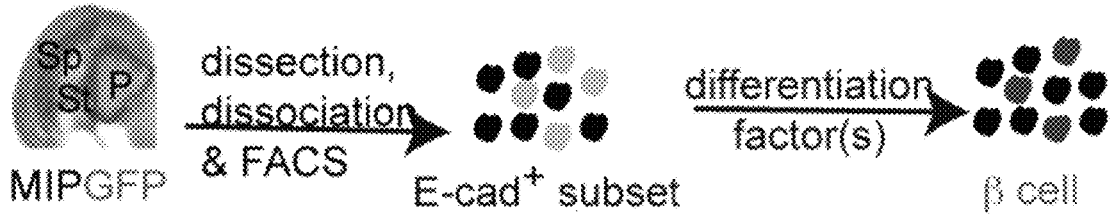
FIG. 1. Nicotinamide promoted insulin-producing cell differentiation from Ngn3$^+$ progenitor-containing E-cad$^+$ cells. (a) Schematic of the strategy used to isolate and differentiate E-cad$^+$ cells. The E15.5 MIPGFP-positive (GFP$^+$) pancreas (P, green), spleen (Sp) and stomach (St) were shown. (b) A representative FACS profile to purify E-cad$^+$ cells. Dissociated pancreatic cells were stained with antibodies to E-cadherin (E-cad), CD45 and TER119 and with propidium iodine (PI), and sorted for PI$^-$CD45TER119$^-$GFP$^-$E-cad$^+$ (E-cad$^+$) and PI$^-$CD45$^-$TER119$^-$GFP$^-$E-cad$^-$ (E-cad$^-$) populations. (c) Time course of insulin-producing cell differentiation. Sorted E-cad$^+$ cells were stimulated with several potential regulators including thyrotropin releasing hormone (TRH), nicotinamide (Nic) and exendin-4 (Ex4) alone or in combination. The number of MIPGFP$^+$ cells was determined. (d) Representative microphotographs of MIPGFP$^+$ cells differentiated from E-cad$^+$ cells with Nic. (e) The dose-response of Nic on insulin-producing cell differentiation. The number of MIPGFP$^+$ cells differentiated in E-cad$^+$ cells at days 4, 6 and 8 in the presence of various concentrations of Nic. (f) The presence of serum in culture medium on insulin-producing cell differentiation. The number of MIPGFP$^+$ cells differentiated in E-cad$^+$ cells at days 4, 6 and 8 in the presence or absence of 10% fetal calf serum (FCS). (g) Insulin-producing cell differentiation in the presence of TRH, Ex4, RA, Notch signaling γ-secretase inhibitors (DAPT, X and XXI), DNA methyltransferase inhibitors (RG-108 and sinefungin) and Wnt signaling regulators (B10 and quercetin) alone or in combination with Nic. The number of MIPGFP$^+$ cells was determined at day 4. For (c) and (e-g), data presented as mean±S.D., n=3, **: p<0.01.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The invention described herein may include one or more range of values (for example, size, displacement and field strength etc.). A range of values will be understood to include all values within the range, including the values defining the range, and values adjacent to the range that lead to the same or substantially the same outcome as the values immediately adjacent to that value which defines the boundary to the range. For example, a person skilled in the field will understand that a 10% variation in upper or lower limits of a range can be totally appropriate and is encompassed by the invention. More particularly, the variation in upper or lower limits of a range will be 5% or as is commonly recognised in the art, whichever is greater.

The present invention is not to be limited in scope by the following specific embodiments. This description is intended for the purpose of exemplification only. Functionally equivalent products, compositions and methods are within the scope of the invention as described herein.

Features of the invention will now be discussed with reference to the following non-limiting description and examples.

Although of paramount importance to a cell replacement therapy for diabetes mellitus, direct differentiation of functional β-like cells from defined pancreatic or islet progenitors in vitro has largely been unsuccessful. Here the inventors describe a unique system in which purified, genetically-tagged mouse islet progenitors efficiently give rise to insulin-producing cells that exhibit many features characteristic of adult β cells, including a similar global gene expression profile. Differentiation was accompanied by the suppression of a range of islet progenitor transcription factors, including Ngn3, Pax4, Isl1 and Myt1. Moreover, these differentiated cells contained insulin secretory granules, were glucose responsive and capable of ameliorating hyperglycemia when transplanted into streptozotocin-treated mice. Application of this differentiation protocol to FACS enriched human islet progenitors generated insulin-producing cells, suggesting the pathways controlling the later steps of β cell genesis is conserved between mouse and human. These data provide insights into islet developmental biology and represents an important step towards a regenerative therapy for diabetes.

The present invention provides a method for generating insulin-producing β-like cells, comprising the steps:
  a) isolating, purifying and/or enriching β-cell progenitor cells from a population of cells;
  b) differentiation of the β-cell progenitor cells into immature insulin-producing β-like cells; and
  c) maturation of the immature insulin-producing β-like cells into mature insulin-producing β-like cells, comprising exposing the immature insulin-producing β-like cells to calcitriol or an analogue thereof.

In an alternate form, the invention resides in the use of insulin-producing β-like cells produced according to the steps of:
  a) isolating, purifying and/or enriching β-cell progenitor cells from a population of cells;
  b) differentiation of the β-cell progenitor cells into immature insulin-producing β-like cells; and
  c) maturation of the immature insulin-producing β-like cells into mature insulin-producing β-like cells, comprising exposing the immature insulin-producing β-like cells to calcitriol or an analogue thereof,
in the manufacture of a medicament for the treatment of diabetes.

The mature insulin-producing β-like cells generated by the method of the invention display features characteristic of functional mature β cells, making them suitable replacements for dead, inactive, or de-differentiated β cells due to a disorder such as diabetes mellitus, when transplanted into a subject in need of such treatment.

Isolating, Purifying and/or Enriching β-cell Progenitor Cells from a Population of Cells A β-cell progenitor cell as referred to herein can comprise any cell or cell population that can differentiate and mature into a mature insulin-producing β-like cell. Examples of β-cell progenitor cells include islet progenitor-like cells given rise from pancreatic precursor cells, fetal pancreas cells and embryonic stem cells, amongst others directly reprogrammed cells. In a preferred form of the invention, the β-cell progenitor cells express the transcription factor Neurogenin3 (Ngn3), Rfx6, Neuro D, Fov or Pax4 or another critical transcription factor. Specifically the β-cell progenitor cells express the transcription factor Neurogenin3 (Ngn3).

The population of cells identified in the method of the invention will be any cell population that includes β-cell progenitor cells. The cell population may comprise more than one type of β-cell progenitor cells. In one non-limiting example, the population of cells may comprise islet progenitor cells and adult dedifferentiated p cells, or another combination of different types of β-cell progenitor cells.

Islet progenitor cells develop from pancreatic progenitors and express a high level of neurogenin 3 (Ngn3, also known as neurog3), a helix-loop-helix transcription factor that is required for the generation of all functional endocrine cells in the pancreas. Partial pancreatic duct ligation in the adult pancreas can reactivate $Ngn3^+$ cells, which, when injected into a fetal pancreas, can differentiate into all islet cell types. Although human pancreas development displays some unique features compared to the mouse, NGN3 seems to play an equivalent role in human islet development.

β-cell progenitor cells may be isolated, purified and/or enriched from the population of cells using a variety of techniques. A combination of techniques may also be used to isolate, purify and/or enrich β-cell progenitor cells from the population of cells. In a one embodiment, flow cytometry incorporating cell sorting is used to isolate, purify, and/or enrich a subpopulation of β-cell progenitor cells from the population of cells. Fluorescence-activated cell sorting (FACS) may also be used to isolate, purify, and/or enrich a subpopulation of β-cell progenitor cells from the population of cells.

Other techniques for isolating, purifying and/or enriching the β-cell progenitor cells include cell separation techniques based on physiochemical properties comprising, any one or more of: size, volume, density, light scatter properties, membrane potential, pH, electrical impedance, electrical charge, and the cell contents in several compounds such as nucleic acids, enzymes, and other proteins; techniques based on affinity (chemical, electrical, or magnetic); techniques based on functional properties of the cell including: adherence, affinity and growth characteristics; or combinations of any of the sorting techniques described herein carried out either sequentially or concurrently. The sorting techniques may be grouped into (a) bulk separation, and (b) single-cell sorting methods (particularly for isolating or purifying the β-cell progenitor cells). Reasons for selecting particular sorting techniques may depend on the features of the β-cell progenitor cells when compared to the other cells in the population. For example, cell purity (proportion of β-cell progenitor cells among the sorted fraction), cell recovery (percentage of cells sorted from the total number of wanted cells within the initial fraction), and sorting efficiency obtained using the method. Techniques for cell sorting using bulk separation include cell filtration, elutriation centrifugation and/or sedimentation, cell affinity, cell culture, and cell charge-based methods. Single-cell sorting methods include flow cytometry. The population of cells will contain sufficient numbers of cells that can be sorted using the herein described techniques.

A variety of different cell surface markers may be used to sort cells in the isolation, purification, and/or enrichment of β-cell progenitor cells from a population of cells. Preferably, such cell surface markers will include those present on β-cell progenitor cells including the non-limiting examples, alpha 6 integrin subunit (CD49f), CD133, E-cadherin (E-cad⁺), stem cell antigen-1 (Sca-1), c-Kit, dispatched homologue 2 (Drosophila) (DISP2), and delta/notch-like EGF repeat containing (DNER). More preferably, the cell surface marker(s) used to sort cells will be one or more selected from the group comprising: E-cad⁺, alpha 6 integrin subunit, and/or CD133.

Alternatively, β-cell progenitor cells may be isolated, purified, and/or enriched from a population of cells using one or more cell surface markers not present on β-cell progenitor cells (negative selection). β-cell progenitor cells may also be isolated, purified, and/or enriched from a population of cells using one or more cell surface markers not present on β-cell progenitor cells and using one or more cell surface markers present on β-cell progenitor cells. Cell sorting using more than one cell surface marker may be carried out sequentially or concomitantly.

A cell surface marker used to sort the β-cell progenitor cells from a population of cells may be tagged. Such tags are known in the art and may include, in one non-limiting example, a green fluorescence protein (GFP) tag, Red Fluorescent Protein (RFP) or DsRed by way of example.

In one embodiment of the invention, β-cell progenitor cells are isolated, purified and/or enriched from the population of cells by cell sorting using E-cad⁺. In another embodiment of the invention, β-cell progenitor cells are isolated, purified and/or enriched from the population of cells by cell sorting using E-cad⁺ and alpha 6 integrin subunit. In a further embodiment of the invention, β-cell progenitor cells are isolated, purified and/or enriched from the population of cells by cell sorting using E-cad⁺, alpha 6 integrin subunit, and CD133. Using multiple markers to isolate, purify, and/or enrich the β-cell progenitor cells from the population of cells may be carried out concomitantly or sequentially.

The β-cell progenitor cells isolated from the population of cells are preferably collected in a suspension of dissociated cells. Methods for culturing and maintaining the isolated, purified, and/or enriched β-cell progenitor cells are known in the art.

Differentiation of the β-cell Progenitor Cells into Immature Insulin-Producing β-like Cells After β-cell progenitor cells have been isolated, purified, and/or enriched from the population of cells, the β-cell progenitor cells are differentiated into immature insulin-producing β-like cells. Differentiation may be induced by a variety of factors. Differentiation may be induced by changes to the expression of genes in the β-cell progenitor cells and/or by modification of cell signalling pathways in the cells and/or by gaining function of glucose-stimulated insulin secretion.

In a preferred form of the invention, inhibiting silent information regulator transcript 1 (Sirt1) initiates and drives differentiation of the β-cell progenitor cells.

Inhibition of Sirt1 in β-cell progenitor cells may be carried out using a variety of different means. This may include reducing or blocking expression of the Sirt1 gene in the β-cell progenitor cells. Alternatively, a chemical inhibitor may be used to inhibit Sirt1 in these cells. Some non-limiting examples of chemical inhibitors include: the reverse amide Salermide which has strong inhibitory effects on Sirt1; Sirt1 Inhibitor IV, (S)-35; Sirt1/2 Inhibitor IV; Cambinol; and/or Isonicotinamide or an analogue thereof. In a preferred embodiment of the method of the invention, nicotinamide or an analogue thereof is used to inhibit Sirt1 in the β-cell progenitor cells.

The concentrations and doses of chemical inhibitors that can be added to the β-cell progenitor cells will be determined by one skilled in the art depending upon, for example, the number of cells, the volume of liquid the cells are situated in, delivery format, and desired dosage required to achieve differentiation of the cells.

β-cell progenitor cells are exposed to nicotinamide and/or another inhibitor of Sirt1 preferably by adding the nicotinamide or an analogue thereof and/or other Sirt1 inhibitor compound to the cell culture medium containing the cells. Preferably, a concentration of nicotinamide or an analogue thereof between 5 mM and 30 mM is added to the cell culture medium to inhibit Sirt1 in the β-cell progenitor cells. More preferably, a concentration of nicotinamide or an analogue thereof between 7 mM and 15 mM is added to the cell culture medium to inhibit Sirt1 in the β-cell progenitor cells. More preferably, a concentration of nicotinamide or an analogue thereof of 10 mM is added to the cell culture medium to inhibit Sirt1 in the β-cell progenitor cells.

Analogues of nicotinamide may include substituted isonicotinamide, or nicotinamides such as 6-substituted nicotinamides. 6-substituted nicotinamide may include substituents such as alkyl, aryl, phosphoaryl or acyl of 1 to 9 carbon atoms, a salt form or an ester form of 1 to 9 carbon atoms of the acyl group. Specific examples of 6-substituted nicotinamides include 6-acetylamino nicotinamide, 6-benzoylamino nicotinamide, 6-oxalylamino nicotinamide and its salts, 6-malonylamino nicotinamide and its salts, 6-succinylamino nicotinamide and its salts, 6-glutarylamino nicotinamide and its salts, 6-succinylamino nicotinamide methyl ester, 6-glutarylamino nicotinamide methyl ester, 6-succinylamino nicotinamide ethyl ester, 6-succinylamino nicotinamide isoamyl ester, 6-glutarylamino nicotinamide ethyl ester, 6-glutarylamino nicotinamide isoamyl ester, 6-maleylamino nicotinamide and its ester, 6-phthalylamino nicotinamide and its ester, 6-phosphorylamino nicotinamide and its ester and 6-diphenylphosphorylamino nicotinamide and its ester.

Analogues of nicotinamide may include substituted 6-aminonicotinamides such as 1-substituted 6-aminonicotinamides. 1-substituted 6-aminonicotinamide may include substituents such as alkyl or aryl of 1 to 9 carbon atoms.

Analogues of nicotinamide may include 1,6-disubstituted 1,6-dihydronicotinamide. 1,6-disubstituted 1,6-dihydronicotinamide may include substituents such as alkyl, aryl or acyl of 1 to 9 carbon atoms. Specific examples of 1,6-disubstituted 1,6-dihydronicotinamides include 1-methyl-6-keto-1,6-dihydronicotinamide, 1-methyl-6-keto-1,6-dihydronicotinic acid, methyl 1-methyl-6-keto-1,6-dihydronicotinate, ethyl 1-methyl-6-keto-1,6-dihydronicotinate, 1-phenyl-6-keto-1,6-dihydronicotinamide, 1-phenyl-6-keto-1,6-dihydronicotinic acid, methyl 1-phenyl-6-keto-1,6-dihydronicotinate, ethyl 1-phenyl-6-keto-1,6-dihydronicotinate, 1-benzyl-6-keto-1,6-dihydronicotinamide, 1-benzyl-6-keto-1,6-dihydronicotinic acid, methyl 1-benzyl-6-keto-1,6-dihydronicotinate, ethyl 1-benzyl-6-keto-1,6-dihydronicotinate, 1-methyl-6-imino-1,6-dihydronicotinamide, 1-phenyl-6-imino-1,6-dihydronicotinamide, 1-benzyl-6-imino-1,6-dihydronicotinamide, methyl 1-methyl-6-imino-1,6-dihydronicotinamide, methyl 1-phenyl-6-imino-1,6-dihydronicotinamide, methyl 1-benzyl-6-imino-1,6-dihydronicotinamide.

Analogues of nicotinamide may include 1-substituted-6-amino-1,2-dihydronicotinamide. 1-substituted-6-amino-1,2-dihydronicotinamide may include substituents such as alkyl, aryl or acyl of 1 to 9 carbon atoms. Specific examples of 1-substituted-6-amino-1,2-dihydronicotinamides include 1-methyl-6-amino-1,2-dihydronicotinamide, 1-methyl-6-amino-1,2-dihydronicotinic acid, methyl 1-methyl-6-amino-1,2-dihydronicotinate, ethyl 1-methyl-6-amino-1,2-dihydronicotinate, 1-phenyl-6-amino-1,2-dihydronicotinamide, 1-phenyl-6-amino-1,2-dihydronicotinic acid, methyl 1-phenyl-6-amino-1,2-dihydronicotinate, ethyl 1-phenyl-6-amino-1,2-dihydronicotinate, 1-benzyl-6-amino-1,2-dihydronicotinamide, 1-benzyl-6-amino-1,2-dihydronicotinic acid, methyl 1-benzyl-6-amino-1,2-dihydronicotinate, ethyl 1-benzyl-6-amino-1,2-dihydronicotinate.

Analogues of nicotinamide may include substituted or unsubstituted thionicotinamide or pyrazinamide.

Maturation of the Immature Insulin-Producing β-Like Cells into Mature Insulin-Producing β-Like Cells, Comprising Exposing the Cells to Calcitriol or an Analogue Thereof In the method for generating insulin-producing β-like cells, 1, 25 (OH)2 vitamin D3 (calcitriol) or an analogue thereof is used for maturating the immature insulin-producing β-like cells into mature insulin-producing β-like cells that display features characteristic of functional mature β cells. The immature insulin-producing β-like cells are exposed to calcitriol or an analogue thereof, which initiates maturation of the cells to become functional, mature insulin-producing β-like cells.

Mature insulin-producing β-like cells produced by the method of the present invention may be identical or substantially identical to mature insulin-producing β cells produced in the body of an animal such as a human. Alternatively, the mature insulin-producing β-like cells produced by the method of the present invention may vary in some way from mature insulin-producing β cells produced in the body of an animal such as a human. In one non-limiting example, the β-like cells may display many or most of the cell surface markers usually present on β cells produced in the human body but some markers may not be present and some different markers not usually present on human β cells may also be present.

An analogue of calcitriol will include both structural and functional analogues and when immature insulin-producing β-like cells are exposed to said analogue, the cells will undergo maturation to become functional mature insulin-producing β-like cells. Such mature insulin-producing β-like cells are preferably capable of producing and storing insulin within the cells, and/or secreting insulin into the cells extracellular environment.

In addition to calcitriol or an analogue thereof, the immature insulin-producing β-like cells may also be exposed to other compounds and/or conditions, which will assist or benefit the maturation of the cells to become mature insulin-producing β-like cells. This may include appropriate growth conditions in suitable media for growth and maturation of β cells that will be known to a person skilled in the art.

Immature insulin-producing β-like cells are exposed to calcitriol or an analogue thereof preferably by adding calcitriol or an analogue thereof to the cell culture medium containing the cells. It is preferable to first remove cell culture medium containing nicotinamide or an analogue thereof from the cells before the maturation step in the method of the invention. Preferably, the concentration of the calcitriol or an analogue thereof in the cell culture medium containing the immature insulin-producing β-like cells is between 1 nM and 100 nM. More preferably, the concentration of the calcitriol or an analogue thereof in the cell culture medium containing the immature insulin-producing β-like cells is between 5 nM and 30 nM. More preferably, the concentration of the calcitriol or an analogue thereof in the cell culture medium containing the immature insulin-producing β-like cells is approximately 10 nM.

The classical role of calcitriol is for the calcium and phosphorus homeostasis. The calcitriol concentration required for the latter is 100-1000-fold lower than that for other roles, potentially complicating the in vivo studies of its roles due to hypercalcaemia. This could be at least partially the cause why there were inconsistent results for other purposes in the literature. Ideally, in order to avoid or minimise any side-effect for in vivo studies and smoothen the pathway towards a clinical trial in the future, a calcitriol analogue which has no or minimal calcemic effect should be used. Preferably the analogue is a non-calcemic calcitriol known as inecalcitol. Inecalcitol is a 19-nor-14-epi-23-yne calcitriol with 480-fold less hypercalc.

It will be appreciated that the hydroxyl substituents at positions 1 and 3 of the A-ring calcitriol and analogues thereof may be such that the analogues are either in the (−) i.e. 1α, 3β or the (+) i.e. (1β, 3α) diastereomic configuration.

Analogues of calcitriol may include those compounds maintaining the 1α-hydroxyl A-ring characteristic of calcitriol, differing in the substituents attached to the D-ring of the steroid framework. The substituents attached to the D-ring of the steroid framework may include ether units such as 22-oxa or 23-oxa. The substituents attached to the D-ring of the steroid framework may alkane, alkene and alkyne units. C25 may be halogenated or replaced by sulfone. C25 may include alkyl, acyl or aryl.

The analogues of calcitriol include compounds which have 23-oxa-25-sulfone, 20-epi-22-oxasulfone, 16-ene-alkenyl sulfone, 16-en-22-oxa and 22E, 24E diene sulfone units Analogues of calcitriol may include cholecalciferol, maxacalcitol, tacalcitol, secalciferol, alfacalciferol and seocalcitol, calcipotriene and inecalcitol and analogues thereof such as 1α, 25dihydroxy-16-ene-23-yne-26,27-hexafluoro-cholecalciferol According to the method of the invention the inventors employed fluorescence reporter and lineage-tracing mouse lines to purify Ngn3$^+$ islet progenitors, enabling differentiation to be easily monitored. Using a modified and optimized version of their previously reported in vitro differentiation system, they identified key signals required for the conversion of Ngn3$^+$ progenitors into functional β cells. In doing so, they provide conclusive evidence that purified Ngn3$^+$ islet progenitors can give rise to insulin-producing cells that are similar to adult β cells at the levels of global gene expression, ultrastructure and function. During differentiation, a range of islet progenitor transcription factor genes, including Ngn3, Pax4, Isl1 and Myt1 was dramatically suppressed. Importantly, the same differentiation system could be used to differentiate an enriched population of human islet progenitors into insulin-producing cells.

Analysis

Prior to transplantation into a subject, the mature insulin-producing β-like cells may be analysed in vitro to confirm the cells present display features characteristic of functional mature β cells including demonstrating glucose-responsive insulin-producing and secreting capability.

The mature insulin-producing β-like cells may be analysed for specific markers including cell surface markers, which provide an indication as to the type of cells present and their levels of maturation. For example, Pdx1, MafA, NeuroD, Nkx6.1 as well as Glut2. Ngn-3, Nkx2.2, Isl-1, Hnf-3 beta, Pax4, and Pax6.

The insulin release from the mature β-like cells is preferably comparable to that of healthy islet cells from a non-diabetic animal (of the same species as the subject into which the mature insulin-producing β-like cells will be transplanted) in response to both low and high glucose levels. For example, mature human insulin-producing β-like cells obtained by the method of the invention will preferably release comparable levels of insulin to that of healthy human islet cells as can be determined by a skilled person, for example, in response to approximately 2.75 mM glucose (basal dose) and approximately 27.5 mM glucose (stimulating dose).

Transplantation

Mature insulin-producing β-like cells generated using the method of the invention may desirably be suitable for transplantation into a subject requiring such cells for treatment of a disease such as diabetes mellitus. The β cells of the subject in need of such treatment may be completely destroyed and/or have critical levels of dead, inactive and/or de-differentiated β cells which are unable to produce sufficient quantities of insulin to maintain homeostasis in the subject. Replacement therapy involving transplanting mature insulin-producing β-like cells generated by the method of the invention into the subject can result in increased insulin production in the subject creating glucose homeostasis. Preferably, the mature insulin-producing β-like cells are transplanted into the pancreas, kidney, portal vein of liver, and/or lymph nodes of the subject. Methods for transplanting the cells into the subject will be known to those skilled in the art. Some non-limiting examples include trans-portal vein injections or trans-lymph node injections.

The transplantation of mature insulin-producing β-like cells obtained by the method of the invention into a subject will preferably ameliorate hyperglycaemia.

The subject into whom the mature insulin-producing β-like cells generated by the method of the invention are transplanted is preferably a human subject. Alternatively, the subject may be another animal such as a non-human mammal.

The invention thereby also provides a method of treating a subject with diabetes mellitus, comprising transplanting the subject with mature insulin-producing β-like cells obtained by a method described herein.

Re-Differentiation of β Cells

Without wanting to be bound by theory, Type 2 diabetes mellitus involves a decrease or loss of glucose stimulated insulin production, storage and secretion in functioning mature β cells of a human or other mammal. This is understood to be the result of de-differentiation of the functional mature insulin-producing β cells even as far as returning to an islet-progenitor-like state. These islet-progenitor-like cells can have expression of Ngn3 or another transcription factor.

The present invention provides a method of treating a subject with diabetes mellitus, including Type 2 diabetes mellitus, comprising one or both of the steps:
  a) inhibiting Sirt1 in β cells of the subject;
  b) exposing β cells of the subject to calcitriol or an analogue thereof;
wherein the β cells of the subject are preferably de-differentiated β cells, including cells de-differentiated back to an islet-progenitor-like state. These one or both steps are preferably performed in the subject, in vivo. Preferably the subject is a human subject.

The steps of inhibiting Sirt1 in the β cells of the subject and exposing β cells of the subject to calcitriol or an analogue thereof is preferably performed as described herein. The selection of one or both of the steps will be determined based upon the de-differentiated state of the β cells. For example, if the β cells have de-differentiated back to an islet-progenitor-like state expressing Ngn3 or another critical islet progenitor marker, then both steps can be performed to generate mature insulin-producing β cells. If de-differentiation of the β cells is to an immature β cell-like state, with the cells that do not have an elevating expression of Ngn3 or another critical islet progenitor marker, then only the second step of exposing the cells to calcitriol or an analogue thereof may be performed to re-store the function of insulin-producing β cells.

The invention provides a mature insulin-producing β-like cell obtained by a method as described herein.

Use

In a further embodiment, the invention extends to the use of the above methods in the manufacture of a medicament for the treatment of insulin related ailments.

Preferably the invention resides in the use of insulin-producing β-like cells produced according to the steps of:
  a) isolating, purifying and/or enriching β-cell progenitor cells from a population of cells;
  b) differentiation of the β-cell progenitor cells into immature insulin-producing β-like cells; and
  c) maturation of the immature insulin-producing β-like cells into mature insulin-producing β-like cells, comprising exposing the immature insulin-producing β-like cells to calcitriol or an analogue thereof,
in the manufacture of a medicament for the treatment of diabetes.

More specifically, the invention is directed in this embodiment to the use of insulin-producing β cells that have been de-differentiated from β cell progenitors or immature β-like cells in the manufacture of a medicament for the treatment of diabetes.

Medicaments produced by the above method are preferably suitable for use in the treatment of diabetes mellitus (e.g. Type 2 diabetes mellitus).

EXAMPLES

Results

Nicotinamide or Analogues Thereof can Promote Insulin-Producing Cell Differentiation from Ngn3$^+$ Progenitor-Containing E-cad$^+$ Population.

Figure 1B:
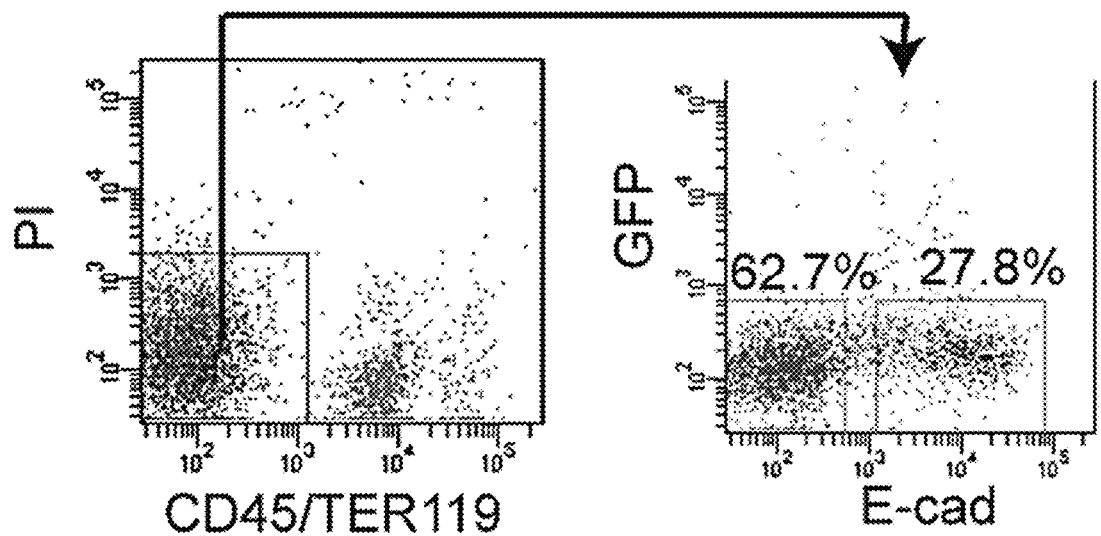
Figure 12:
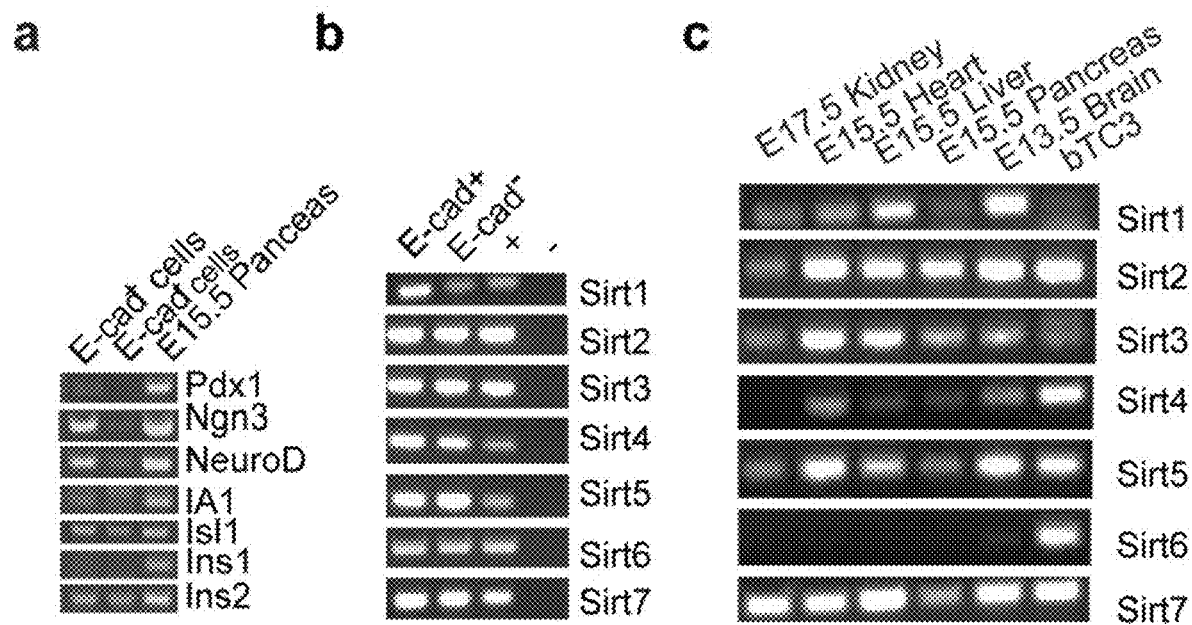
FIG. 12. RT-PCR analyses of developmental cells and tissues. a Islet progenitor gene expression in purified E-cad+ and E-cad− cells. b Sirtuin mRNA transcripts in purified E-cad+ and E-cad− cells. As controls, RNA was extracted from E13.5 brain ("+" control for Sirt1), E15.5 heart ("+" control for Sirt3) and β cell line βTC3 cells ("+" control for remaining sirtuins). c Sirtuin transcripts expressed in a variety of developing tissues. RNA was extracted from E17.5 kidney, E15.5 heart, liver and pancreas, E13.5 brain and the β cell line βTC3 cells.

To monitor insulin-producing cell differentiation in culture, a mouse line was used in which the green fluorescence protein (GFP) tag is expressed under the control of the mouse insulin-1 promoter (hereafter termed MIPGFP mice) (FIG. 1a). The inventors reasoned that, like other foregut endoderm-derived cells, the neurogenin 3-expressing (Ngn3$^+$) islet progenitors should also express E-cadherin (E-cad⁺). Using a fluorescence-activated cell sorter, fetal pancreatic cells were separated into GFP⁻E-cad⁺ (hereafter E-cad⁺) and GFP⁻E-cad⁻ (E-cad⁻) populations (FIG. 1b). As expected, Ngn3 mRNA was highly expressed in the E-cad⁺ but not E-cad⁻ population (FIG. 12a). The expression of Ngn3 protein was confirmed by immunofluorescence staining in the E-cad⁺ population (1-2% of cells). Down-stream effector genes, including NeuroD (neuronal differentiation 1), Ia1 (insulinoma associated 1) and Isl1 (Islet1), were also expressed in E-cad⁺ cells (FIG. 12a). There was no detectable expression (0%) in either population of C-peptide, suggesting that differentiated β cells were completely absent from both sorted populations. Sirt1, but not other sirtuin family genes, was prominently expressed in purified Ngn3⁺ progenitor-containing E-cad⁺ cells (FIG. 12b), and its expression varied in different developing tissues (FIG. 12c).

Figure 2A:
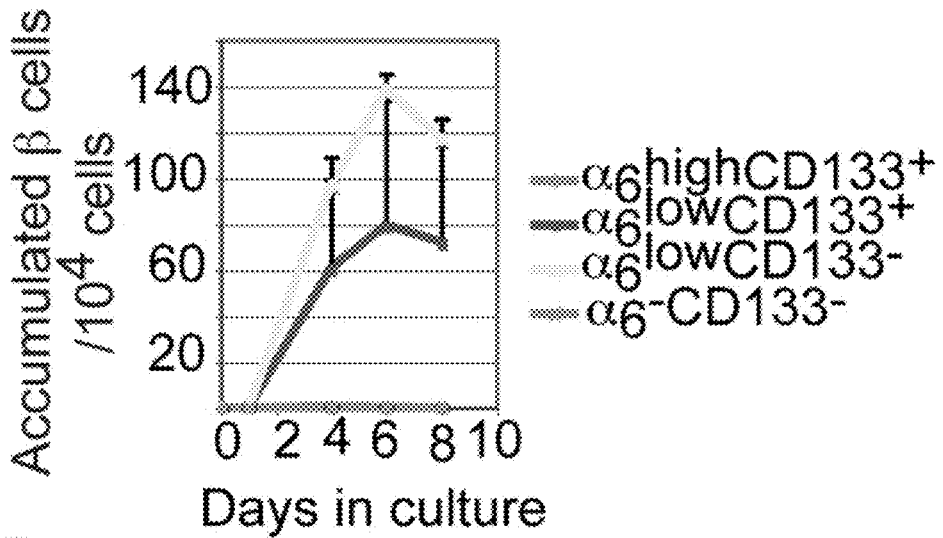
FIG. 2. Markers used to enhance enrichment of Ngn3$^+$ progenitors that differentiated into β-like cells. (A) Time course of β-cell differentiation. Dissociated E15.5 MIPGFP pancreatic cells were stained with antibodies against $\alpha_6$ integrin subunit and CD133. Sorted $\alpha_6^{high}$CD133$^+$, $\alpha_6^{low}$CD133$^+$, $\alpha_6^{low}$CD133$^-$ and $\alpha_6^-$CD133$^-$ cells were all cultured with Nic. The number of GFP$^+$ β cells was determined at various time points (mean±S.D., n=3). (B) Representative FACS profiles to purify Ngn3-enriched cells with monoclonal antibodies against $\alpha_6$ and E-cad. PI$^-$CD45$^-$TER119$^-$GFP$^-\alpha_6^{high}$E-cad$^+$ ($\alpha_6^{high}$E-cad$^+$), PI$^-$CD45$^-$TER119$^-$GFP$^-$ $\alpha_6^{low}$E-cad$^+$ ($\alpha_6^{low}$E-cad$^+$), PI$^-$CD45$^-$TER119-GFP$^-\alpha_6^{low}$E-cad$^-$ ($\alpha_6^{low}$E-cad$^-$) and PI$^-$CD45TER119$^-$GFP$^-\alpha_6^-$E-cad$^-$ ($\alpha_6^-$E-cad$^-$) were sorted. (C) Time course of β-cell differentiation in the four populations in the presence of Nic (mean±S.D., n=3).
Figure 2B:
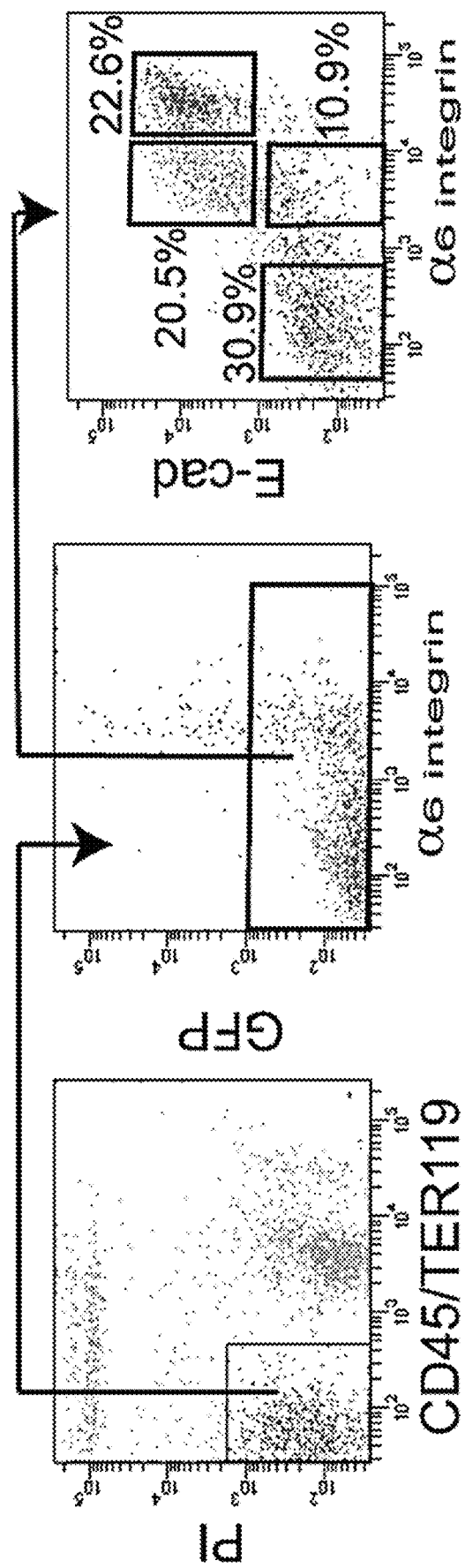
Figure 2C:
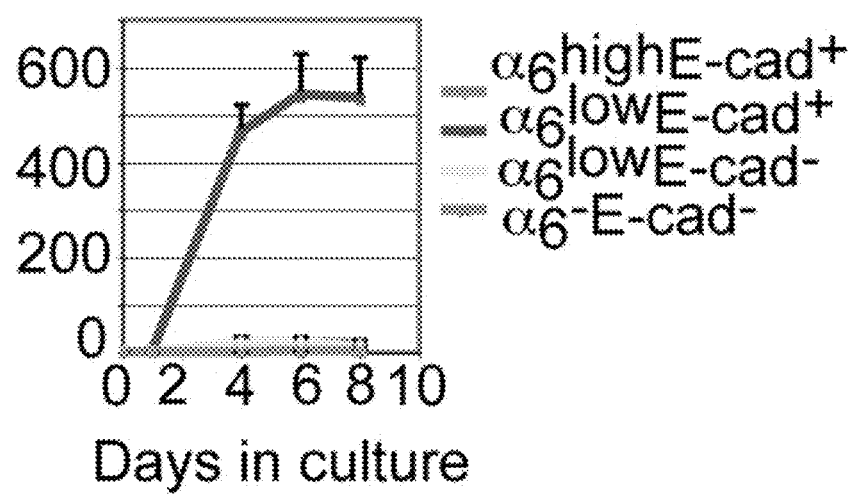

As markers for E-cad and $\alpha_6$ had been successfully used to enrich pancreatic progenitors containing Ngn3⁺ cells, it was reasoned that a combination of antibodies against the two molecules may further enrich these cells. Indeed, PI⁻CD45⁻TER119⁻ GFP⁻$\alpha_6^{high}$E-cad⁺ ($\alpha_6^{high}$E-cad⁺), PI⁻CD45⁻TER119⁻GFP⁻$\alpha_6^{low}$E-cad⁺ ($\alpha_6^{low}$E-cad⁺), PI⁻CD45⁻$^{TER}$119⁻GFP⁻$\alpha_6^{low}$E-cad⁻ ($\alpha_6^{low}$E-cad⁻) and PI⁻CD45⁻TER119⁻GFP⁻$\alpha_6^-$E-cad⁻ ($\alpha_6^-$E-cad⁻) cells could be sorted (FIG. 2B). As expected, only $\alpha_6^{low}$E-cad⁺ cells, but not the remaining populations, differentiated into GFP⁺ β cells with a much higher yield (FIG. 2C), approximately three-fold more than from $\alpha_6^{low}$CD133⁺ or $\alpha_6^{low}$E-cad⁻ population (FIG. 2A).

Figure 1C:
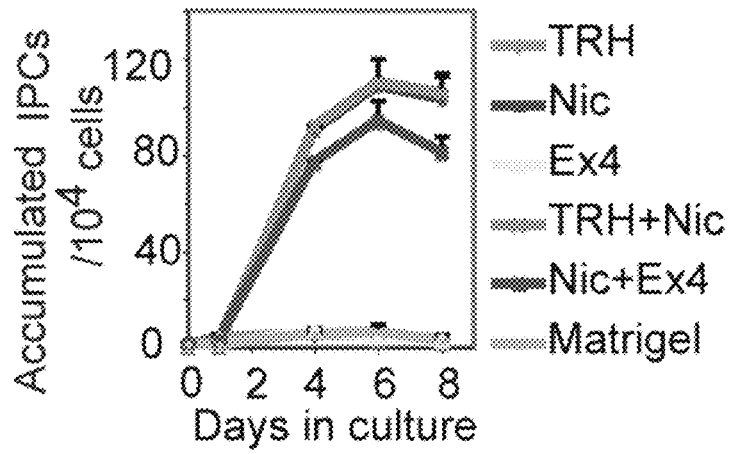
Figure 1D:
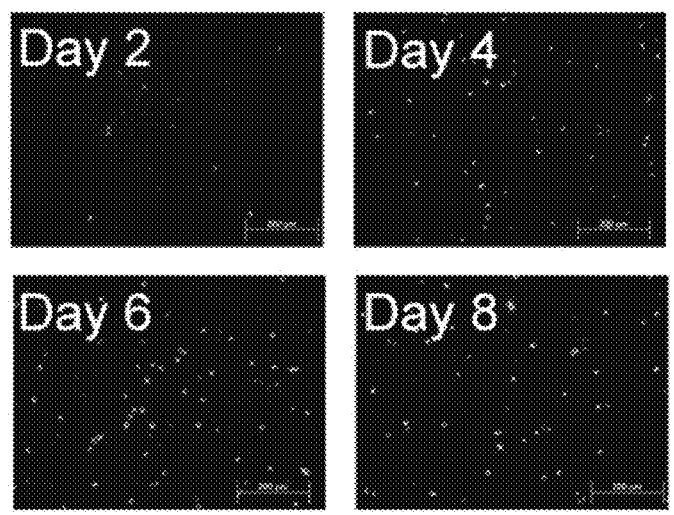
Figure 1E:
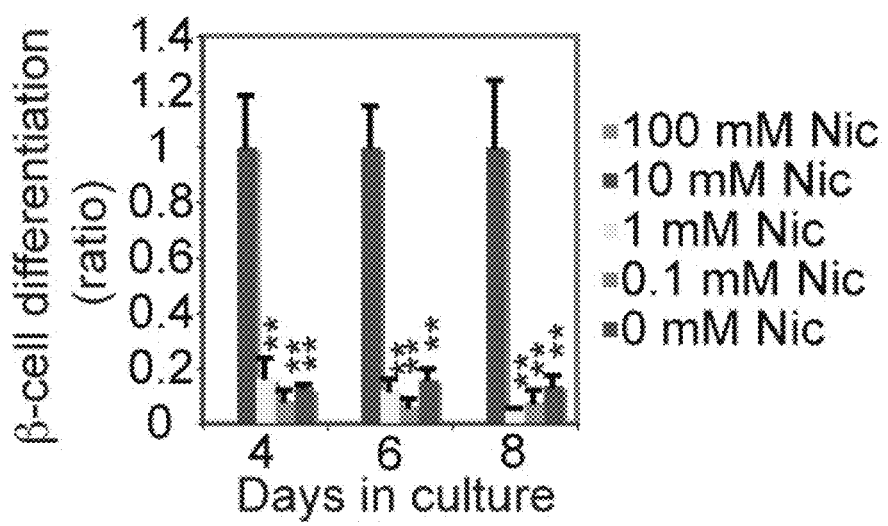
Figure 1F:
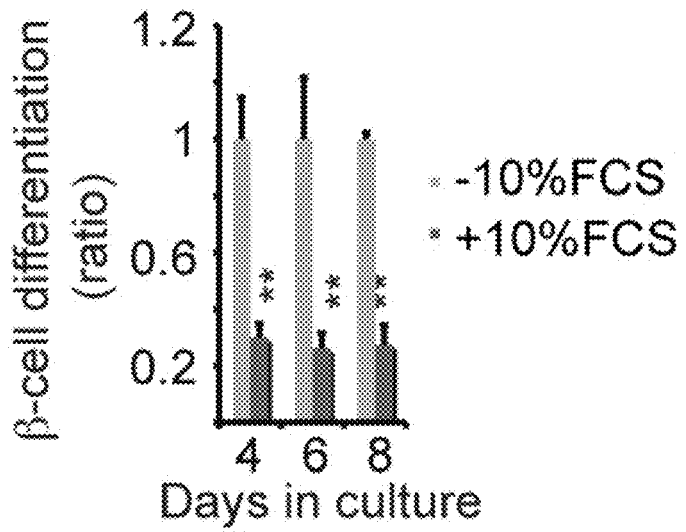
Figure 1G:
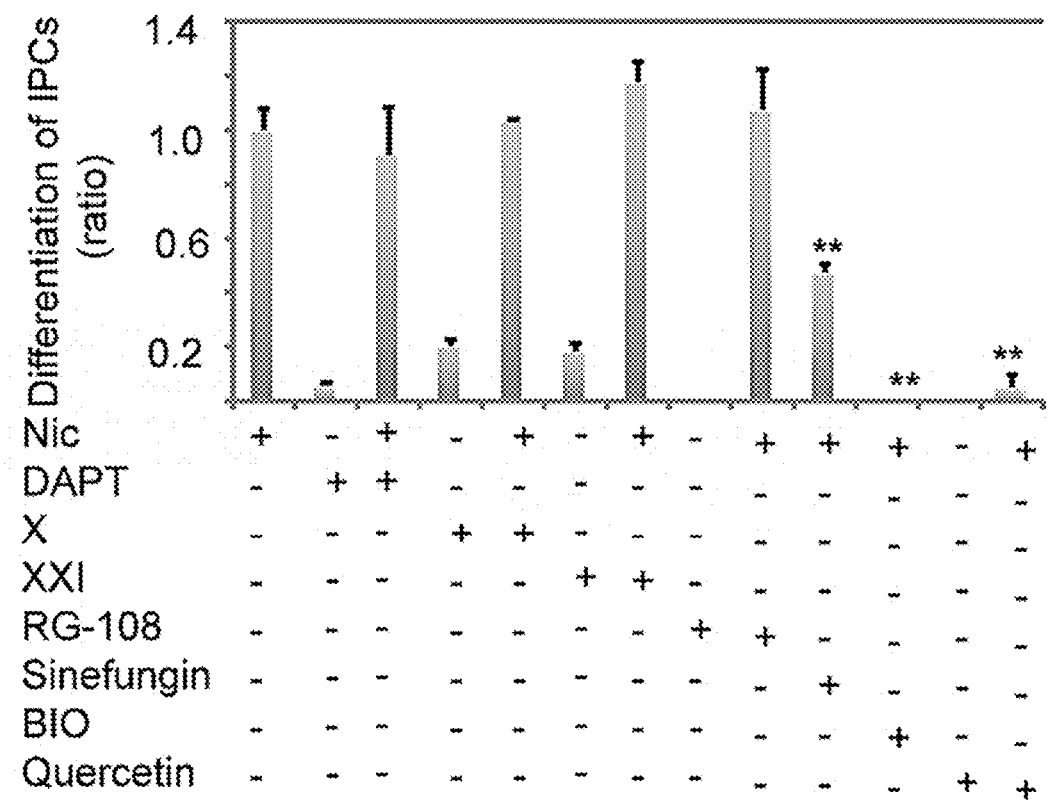

To investigate the role of Sirt1 in Ngn3⁺ progenitors, the E-cad⁺ cells were cultured with the small molecule nicotinamide (Nic), a physiological non-competitive inhibitor of Sirt1, or a dozen other potential regulators, individually or in combination in our serum-free and feeder-free cultures (FIG. 1c-g). Significant numbers of MIPGFP⁺ cells, indicative of insulin-producing cells on the differentiation pathway to β cells, were only produced in the presence of Nic and only in cultures of the E-cad⁺ population. MIPGFP⁺ cells were undetectable at day 0 but appeared by day 2, with a peak at day 6. There were at least 17-fold more MIPGFP⁺ cells in the presence of Nic (FIG. 1c,d). Culture with any of the other molecules, including TRH, retinoic acid, Ex4, (Notch signaling) γ-secretase inhibitor (DAPT, X or XXI), DNA methyltransferase inhibitor (RG-108 or sinefungin) or Wnt signaling regulator (BIO or quercetin) did not yield MIPGFP⁺ cells (FIG. 1g). Furthermore, co-culture with sinefungin, BIO and quercetin suppressed or abolished Nic-induced differentiation. In contrast, culture of E-cad⁻ cells yielded essentially no MIPGFP⁺ cells after any chemical treatment. These data suggest that only in the presence of Nic can the Ngn3⁺ progenitors in the E-cad⁺ population give rise to cells in which the insulin-1 gene was up-regulated.

Figure 5:
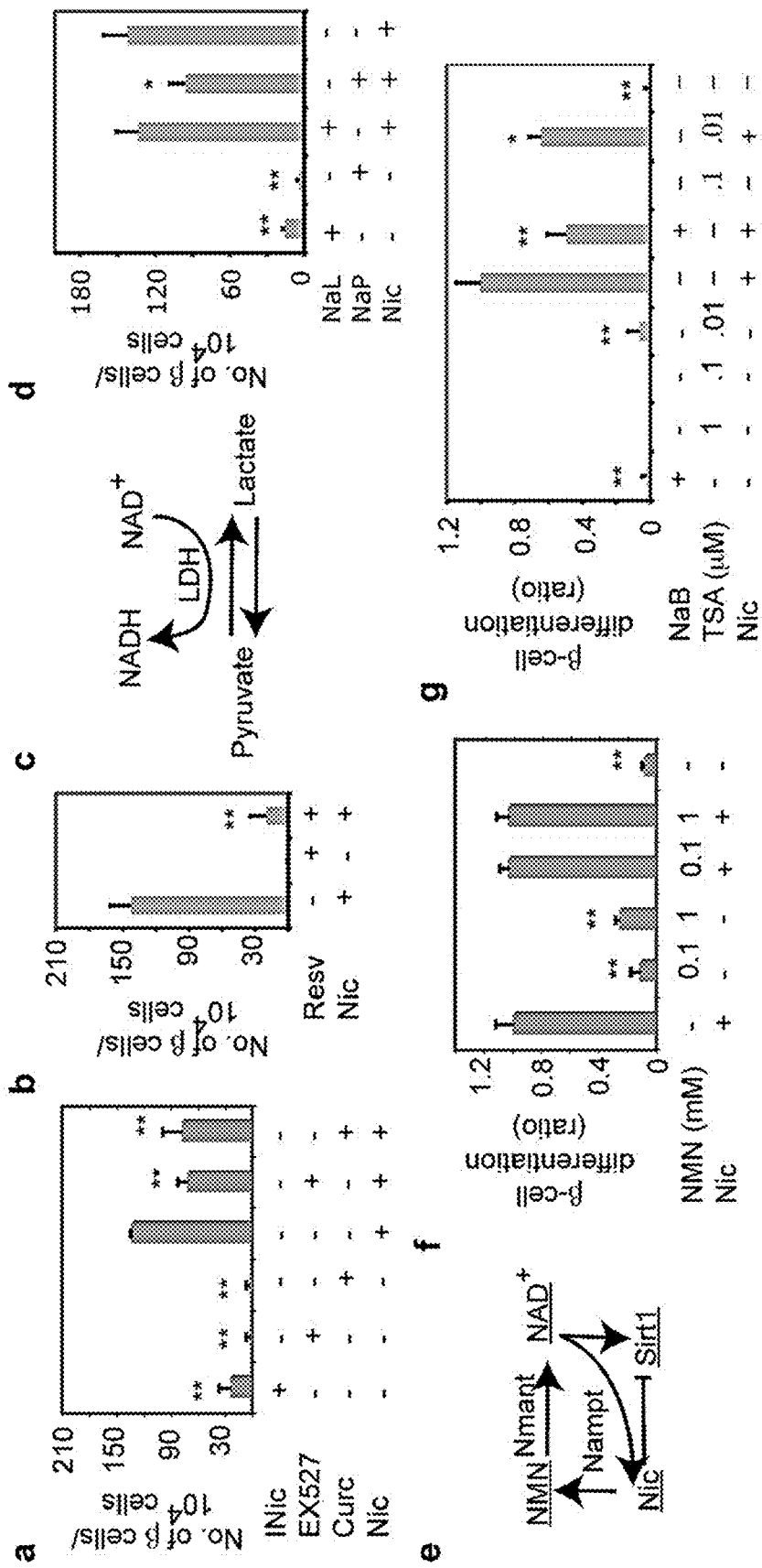
FIG. 5. Molecular basis of nicotinamide effects on β-cell differentiation. (a) Insulin-producing cell differentiation from E-cad+ cells in the presence of iso-nicotinamide (INic), EX527 and curcumin (Curc) alone or in combination with Nic. The number of MIPGFP+ cells was determined at day 4. (b) Insulin-producing cell differentiation from E-cad+ cells at day 4 of culture in the presence of resveratrol (Resv) alone or in combination with Nic. (c) Schematic of how lactate and pyruvate metabolism affects NADH/NAD+ levels catalyzed by lactate dehydrogenase (LDH). (d) Insulin-producing cell differentiation from E-cad+ cells at day 4 in the presence of sodium lactate (NaL) and sodium pyruvate (NaP) alone or in combination with Nic. (e) Schematic of how Nic, nicotinamide mononucleotide (NMN) and NAD+ affect Sirt1 activities. (f) Insulin-producing cell differentiation from E-cad+ cells at day 4 in the presence of NMN alone or in combination with Nic. (g) Insulin-producing cell differentiation from E-cad+ cells at day 4 in the presence of sodium butyrate (NaB) and trichostatin A (TSA) alone or in combination with Nic. Data presented as mean±S.D., n=3. *: p<0.05, **: p<0.01 compared to that in the presence of Nic alone.
Figure 11:
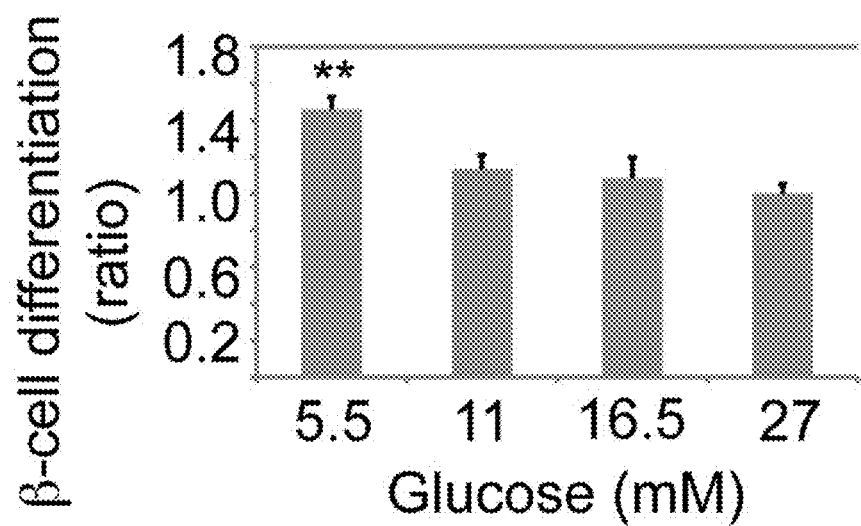
FIG. 11. Normal glucose concentration is optimal for β-cell differentiation of Ngn3+ islet progenitors. Ngn3-GFP+ progenitors were purified from E15.5 Ngn3-GFP/RIP-DsRed mice and cultured in various concentrations of D-glucose as indicated in the presence of Nic (10 mM). The numbers of DsRed+ cells were determined at day 4. Data presented as mean±S.D., n=3. **: p<0.01 compared to other glucose concentrations.
Figure 14:
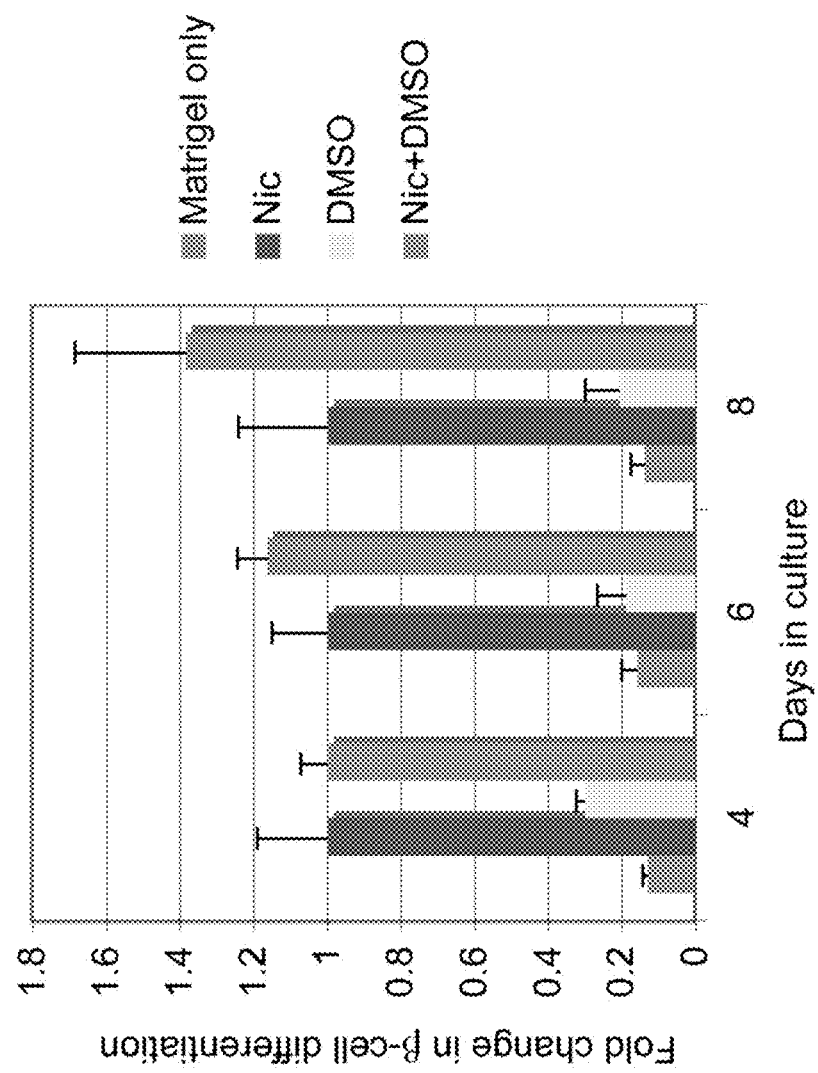
FIG. 14. The solvent dimethyl sulfoxide (DMSO) failed to promote insulin-producing cell differentiation in E-cad+ cells. E-cad+ cells were sorted from dissociated E15.5 MIPGFP mouse pancreas and cultured in the presence of DMSO with or without Nic. Data presented as mean±S.D., n=3.
Figure 15:
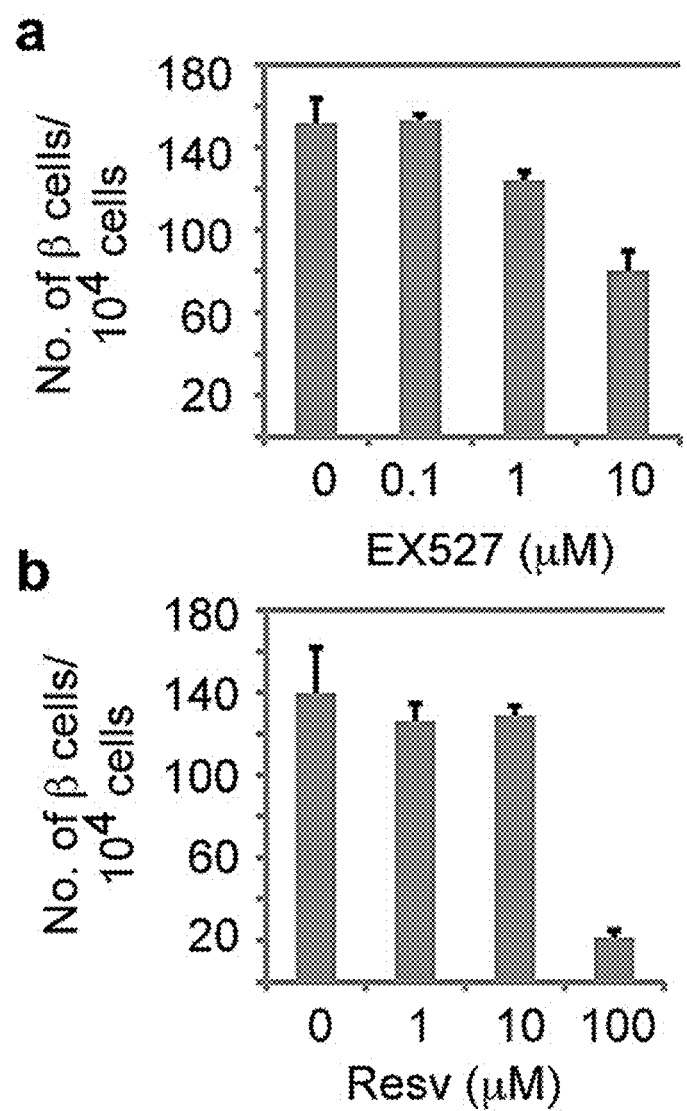
FIG. 15. Dose-responses of EX527 and resveratrol in E-cad+ cells on insulin-producing cell differentiation. E-cad+ cells were sorted from dissociated E15.5 MIPGFP mouse pancreas and cultured for 4 days with various concentrations of EX527 (a) or resveratrol (Resv, b) in the presence of Nic. Data presented as mean±S.D., n=3.

Molecular Basis of Nicotinamide Promotion of Insulin-Producing Cell Differentiation To demonstrate Nic acted via inhibition of Sirt1 and to characterize its underlining mechanism of action, we tested several compounds including chemical analogues, pharmacological inhibitors and metabolic intermediates. Isonicotinamide (INic) is a Nic analogue that inhibits the base-exchange of Sirt1 but not its deacetylation reaction while EX527 is a potent pharmacological inhibitor of only Sirt1 deacetylation chemistry. Insulin-producing cell differentiation from E-cad⁺ cells was significantly lower in INic cultures, which yielded approximately half of the number of MIPGFP⁺ cells at days 4 (FIGS. 5a), 6 and 8 (FIG. 11a), compared to Nic. As a control, the solvent for INic, dimethyl sulfoxide, did not show any effect (FIG. 14). In contrast, EX527 did not significantly promote differentiation on its own, but did reduce Nic-induced differentiation (FIGS. 5a, 11a and 15a). These results suggest that inhibition of base-exchange chemistry is essential, but that concurrent inhibition of the deacetylation reaction also is required for optimal differentiation.

To gain further evidence of the importance of the Sirt1 acetylation chemistry, we tested curcumin, an inhibitor of the HAT p300/CREB-binding protein, which physically interacts with and antagonizes Sirt1. Consistent with the results above, curcumin significantly reduced the Nic-induced differentiation at all time-points to levels similar to INic cultures (FIGS. 5a and 13a).

Figure 13:
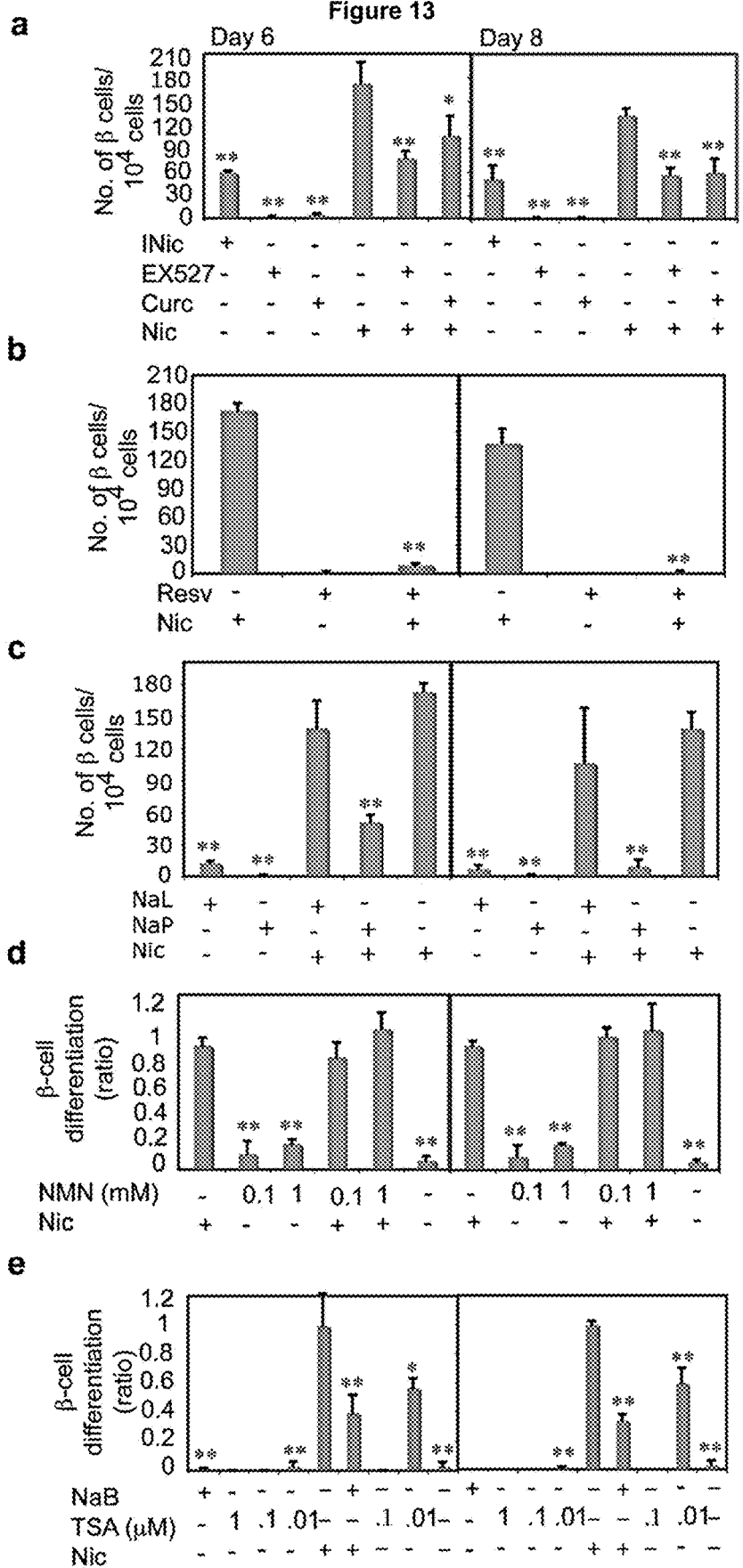
FIG. 13. Molecular analysis of how nicotinamide promotes insulin-producing cell differentiation at days 6 and 8. a Insulin-producing cell differentiation from E-cad+ cells in the presence of iso-nicotinamide (INic), EX527 and curcumin (Curc) alone or in combination with Nic. b Insulin-producing cell differentiation from E-cad+ cells in the presence of resveratrol (Resv) alone or in combination with Nic. c Insulin-producing cell differentiation from E-cad+ cells in the presence of sodium lactate (NaL) and sodium pyruvate (NaP) alone or in combination with Nic. d β-cell differentiation from E-cad+ cells in the presence of nicotinamide mononucleotide (NMN) alone or in combination with Nic. e Insulin-producing cell differentiation from E-cad+ cells in the presence of sodium butyrate (NaB) and trichostatin A (TSA) alone or in combination with Nic. Data presented as mean±S.D., n=3. Non-parametric, unpaired Mann-Whitney U Tests were used to assess statistical significance. *: $p<0.05$, **: $p<0.01$ compared to that in the presence of Nic alone.

Activation of Sirt1 by the polyphenolic resveratrol completely abolished Nic-induced differentiation without apparently affecting cellular viability (FIGS. 5b, 13b and 15b). Increasing the pyruvate/lactate ratio elevates NAD⁺/NADH (reduced form of NAD⁺) ratio (FIG. 5c) and Sirt1 activity, so this should decrease Nic-induced differentiation. Consistent with this prediction, addition of sodium pyruvate significantly inhibited (p<0.01) Nic-induced β-cell differentiation (FIGS. 5d and 11c). Nicotinamide mononucleotide is a metabolic intermediate for the synthesis of NAD⁺ (FIG. 5e) catalyzed by nicotinamide phosphoribosyltransferase, an enzyme that is undetectable in the pancreas. That may be why the presence of a higher concentration of nicotinamide mononucleotide did not modify Nic-induced β-cell differentiation (FIGS. 5f and 13d).

Furthermore, the addition of sodium butyrate or trichostatin A, inhibitors of type I or II HDACs which promote Ngn3⁺ cell specification, significantly (p<0.05) reduced Nic-induced differentiation (FIGS. 5g and 13e), suggesting that such HDACs play an opposing role in β-cell differentiation. Taken together, the above data not only provided supportive evidence but also established a novel method for the inventors to perform the following studies.

Verification that Ngn3+ Progenitors Gave Rise to Insulin-Producing Cells

Figure 6A:
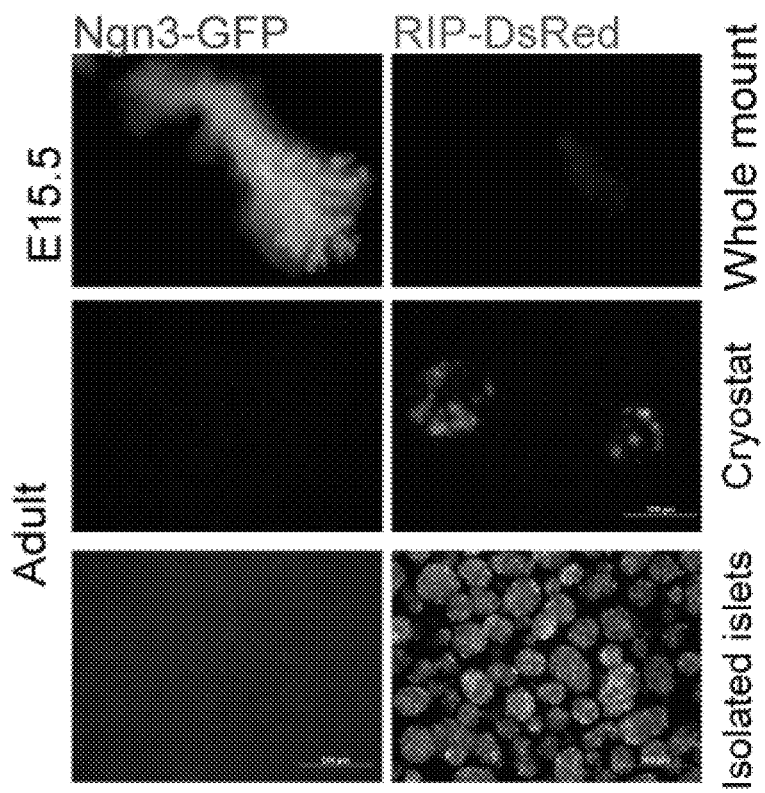
FIG. 6. Verification that Ngnr progenitors gave rise to insulin-producing cells. (a) Representative microphotographs of GFP and DsRed expression in E15.5 and adult Ngn3-GFP/RIP-DsRed mouse pancreas, and isolated islets. (b) Representative FACS profile to purify Ngn3-GFP+ (namely Ngn3+) progenitors. Dissociated E15.5 Ngn3-GFP/RIP-DsRed pancreatic cells were stained with DAPI for FACS. (c) Immunofluorescence analysis of purified Ngn3-GFP+ progenitors. Purified GFP+ cells were stained with antibodies against Ngn3 (red) and with DAPI (blue). (d) Islet progenitor gene expression in purified Ngn3+ progenitors. (e) Real time life imaging analysis during Ngn3+ progenitors (green) giving rise to insulin-secreting DsRed+ cells (red). (f) Representative FACS profiles of the time-course of DsRed+ cell differentiation. Ngn3-GFP+ progenitors were purified, cultured and harvested for FACS analysis at indicated times. (g) Differentiation of different fractions of Ngn3-GFP+ populations. Subpopulations of Ngn3-GFP+ cells were sorted as indicated in (b) and cultured in the presence of Nic. The numbers of DsRed+ cells were determined at day 4. Data presented as mean±S.D., n=3. **: p<0.01 compared to that in the Ngn3-GFP$^{Dim}$ population.
Figure 6B:
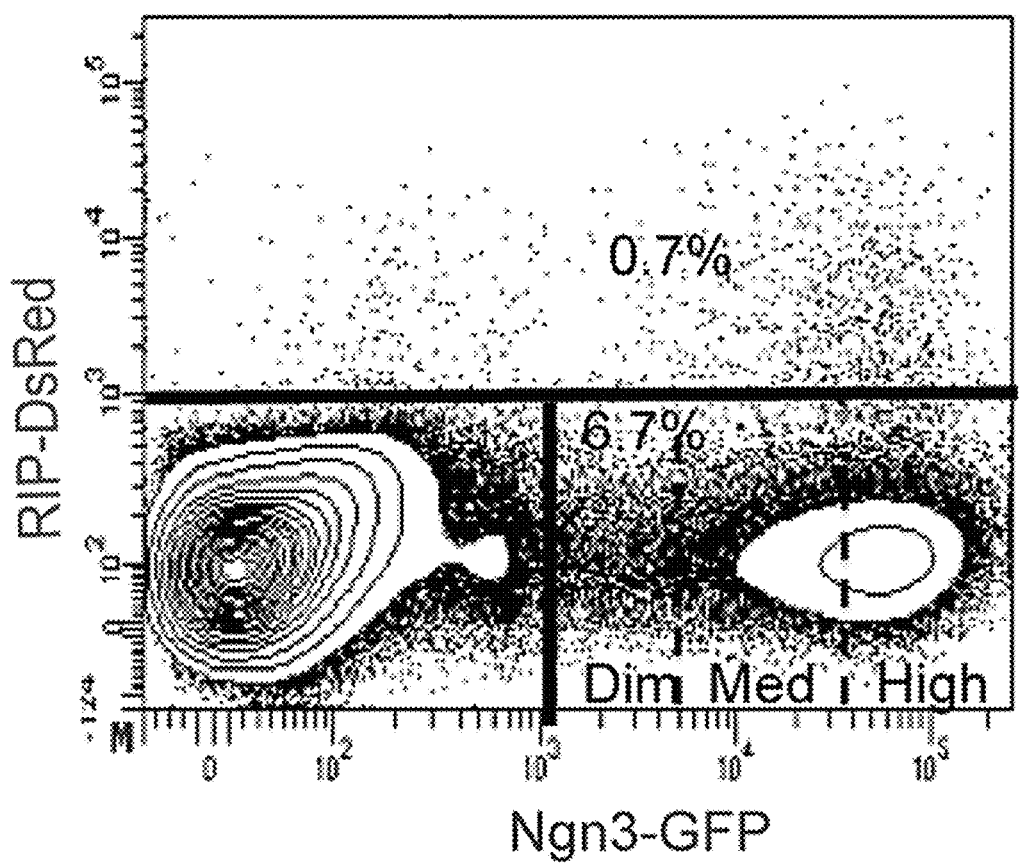
Figure 6C:
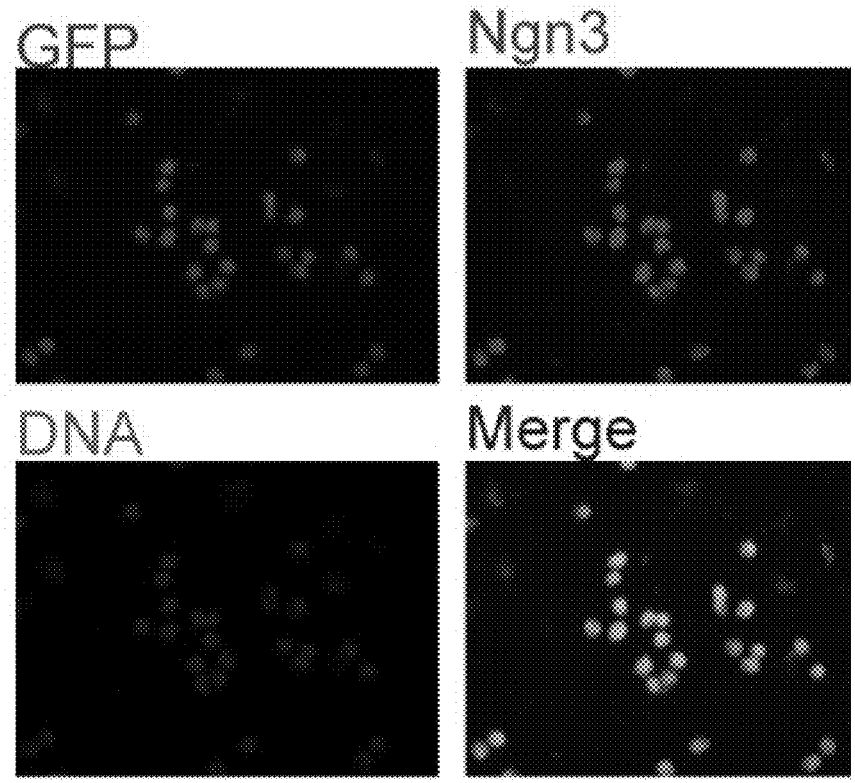
Figure 6D:
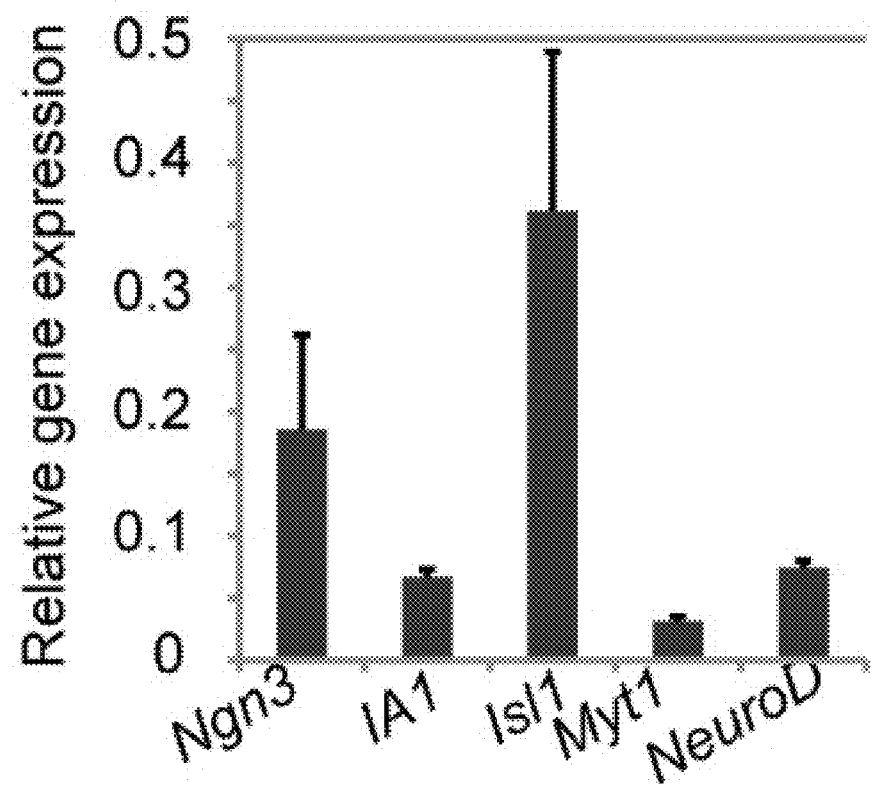
Figure 6E:
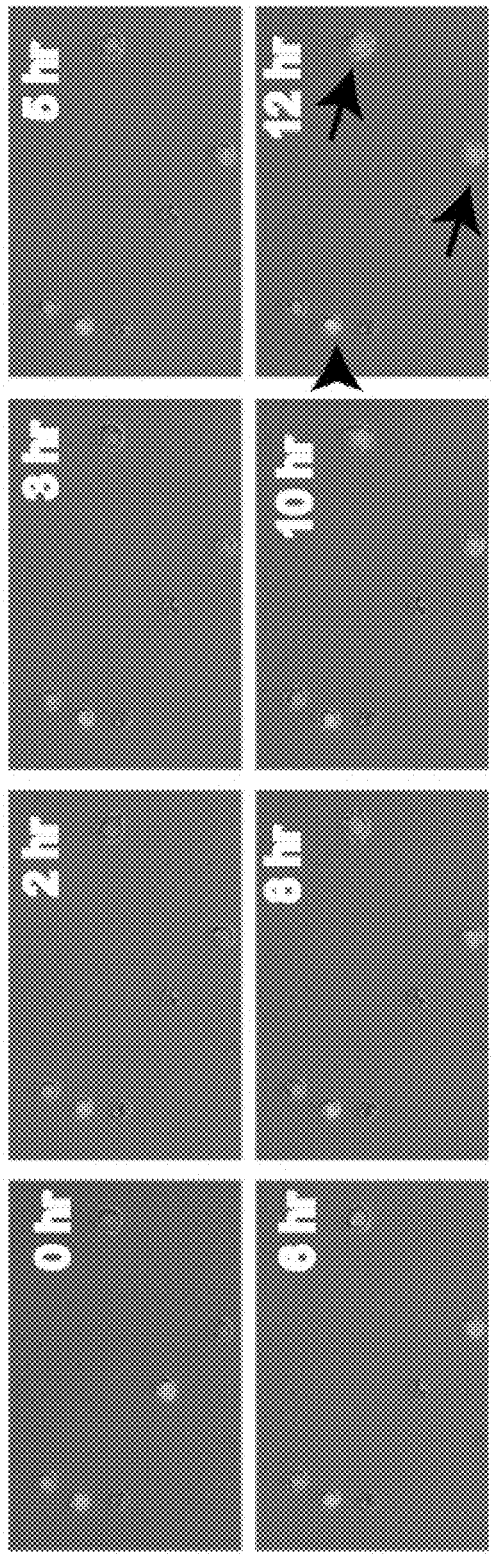
Figure 6G:
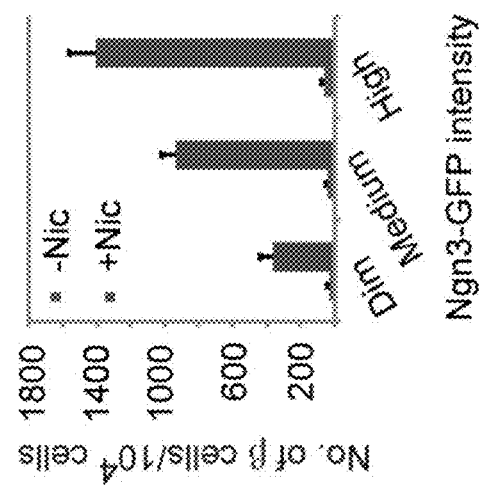
Figure 6F:
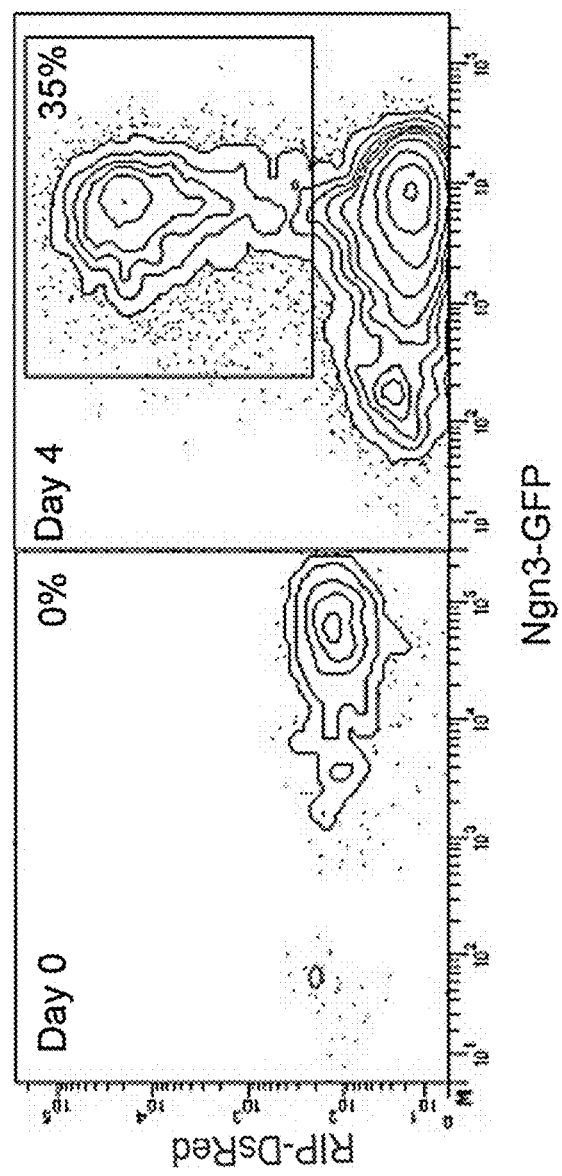
Figure 16:
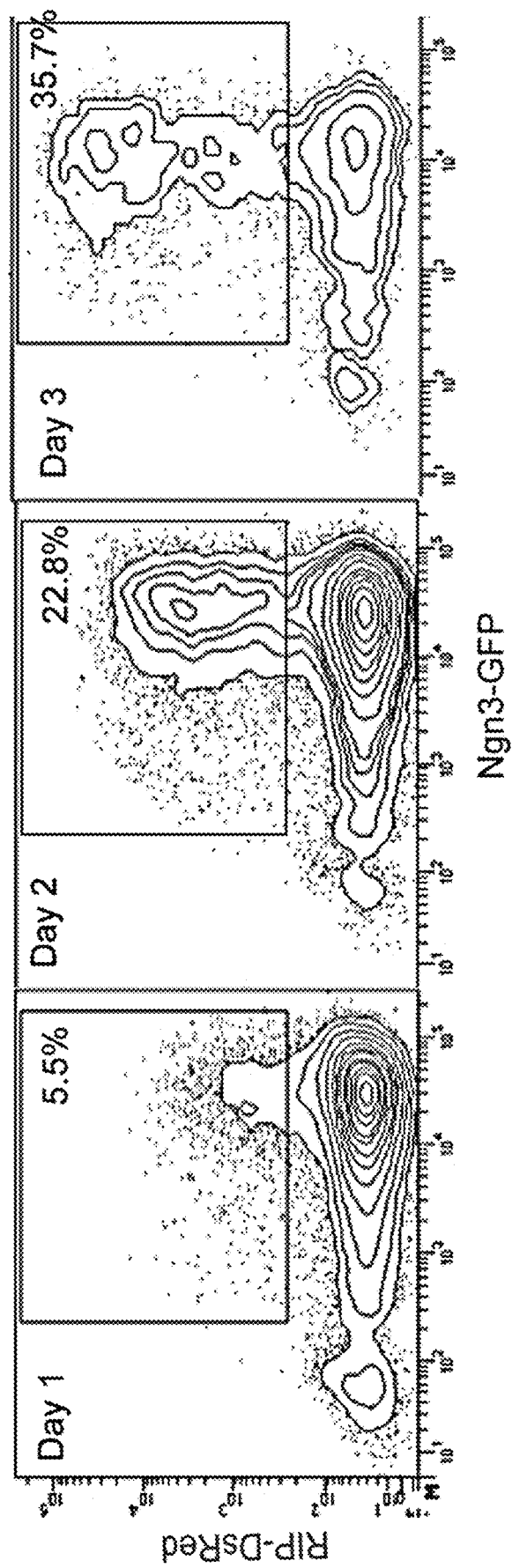
FIG. 16. Representative FACS profiles of the time-course of DsRed+ cell differentiation. Ngn3-GFP* progenitors were purified, cultured and harvested for FACS analysis at indicated times.
Figure 17:
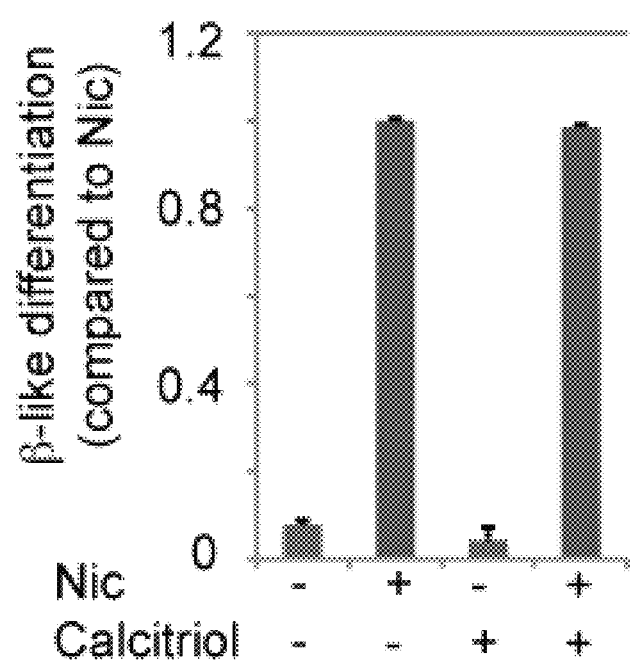
FIG. 17. Calcitriol does not promote β-cell differentiation of Ngn3+ islet progenitors. Ngn3-GFP+ progenitors were purified from E15.5 Ngn3-GFP/RIP-DsRed mice and cultured in the presence of calcitriol (10 nM) with or without Nic (10 mM). The numbers of DsRed+ cells were determined at day 4. Data presented as mean±S.D., n=3. **: $p<0.01$ compared to with Nic.
Figure 18:
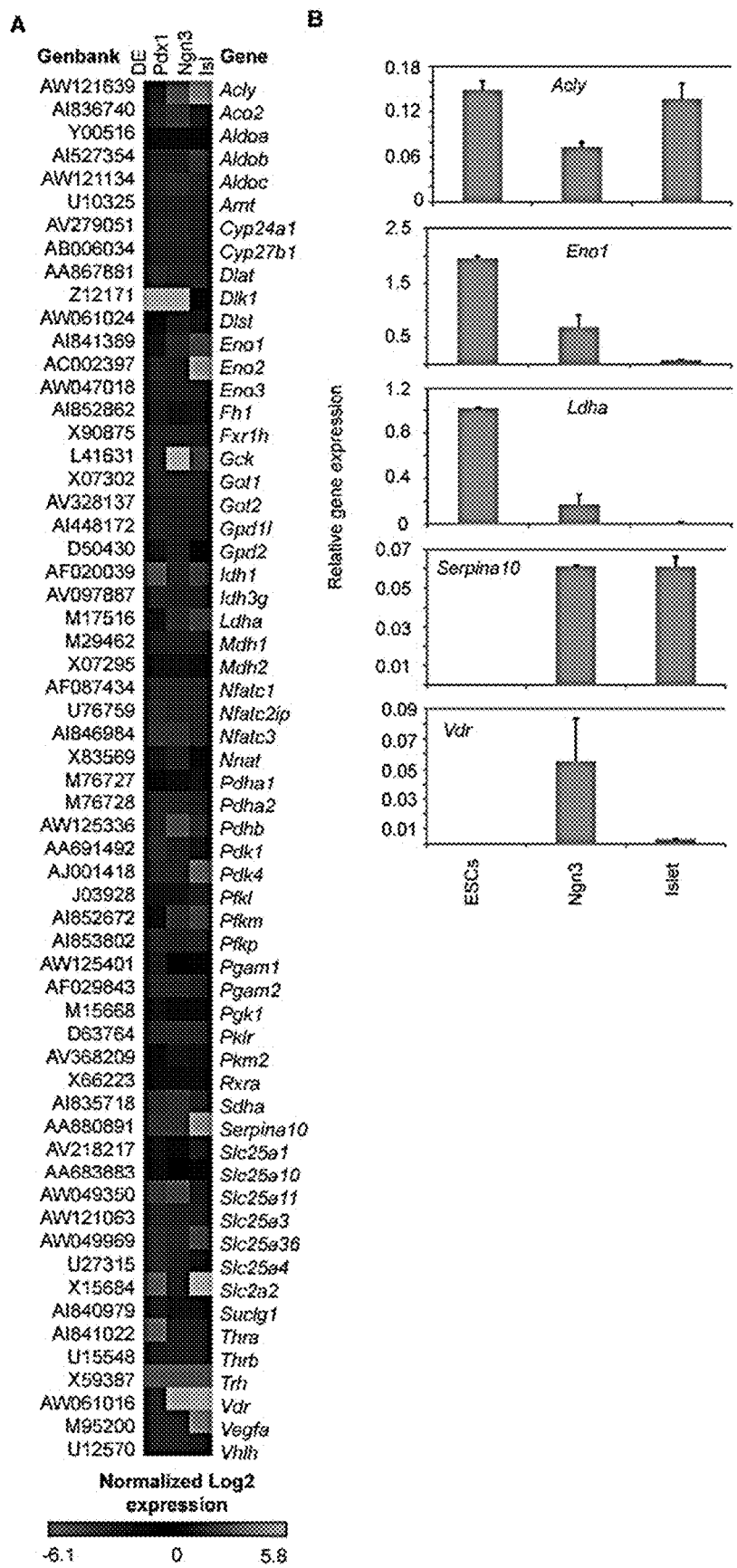
FIG. 18. Identification of five short-listed β-cell maturation factors. (A) Expression heatmap showing a list of 61 genes that encode molecules important for metabolism as potential β-cell maturation factors. The microarray raw datasets were available from a public domain and analysed as we described recently. (B) Quantitative real time RT-PCR analysis of five short-listed genes including the calcitriol nuclear receptor gene Vdr. RNAs were extracted from mouse embryonic stem cells (ESCs), purified Ngn3+ progenitors (Ngn3) and adult islets (Islet), respectively. Gene expression levels were normalised to the internal ribosomal 18s RNA level. Expression values are shown as mean±SD, n=3.
Figure 19:
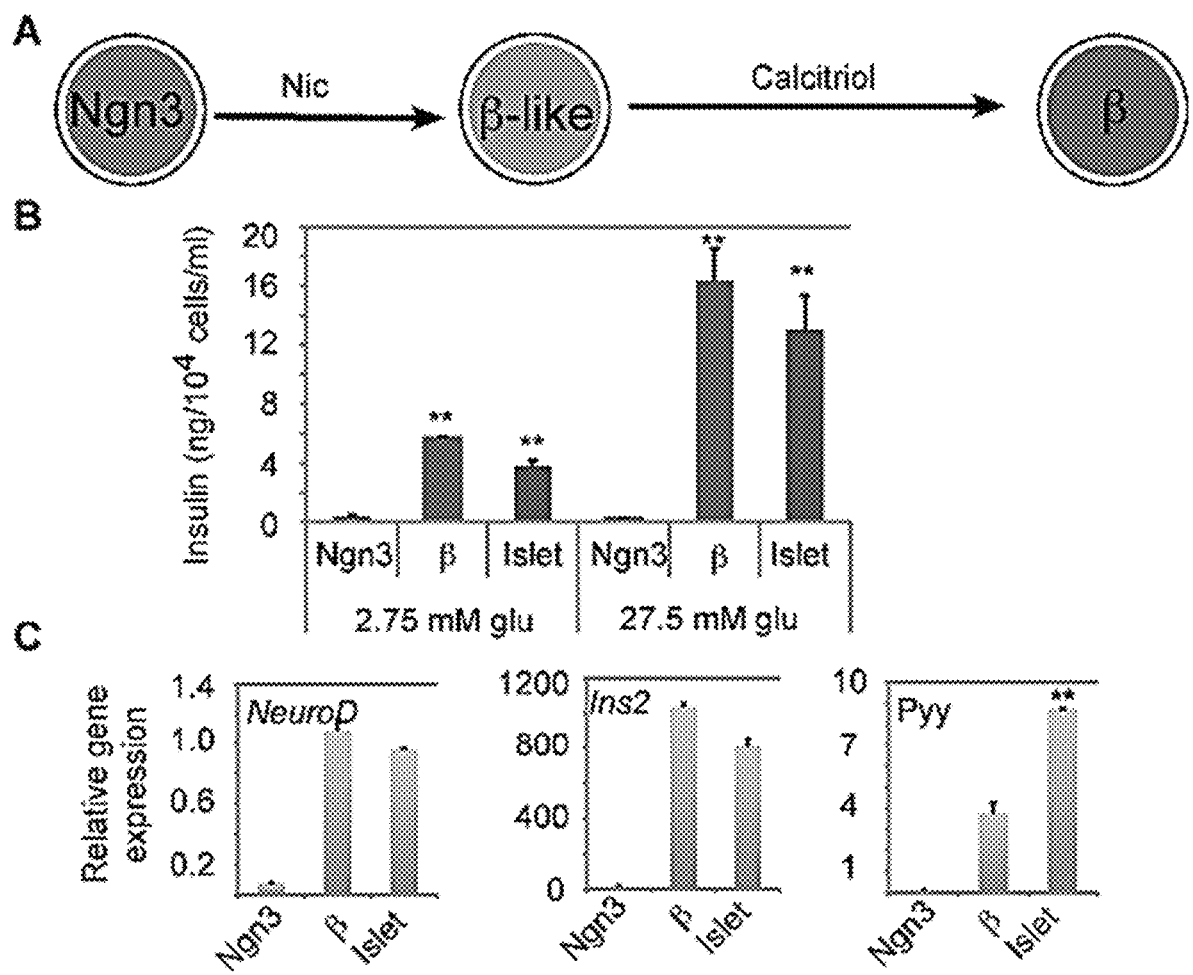
FIG. 19. Calcitriol promoted the maturation of differentiated β-like cells. (A) Strategy to differentiate Ngn3+ progenitors (Ngn3) in the presence of nicotinamide (Nic) into insulin-producing β-like cells (β-like) that are subsequently matured with calcitriol as functional β cells (β). (B) Glucose stimulated insulin secretion analysis. The insulin-producing β-like cells differentiated from Ngn3-FP* progenitors were treated with calcitriol (10 nM) gave rise to functional β cells (β). Uncultured Ngn3+ progenitors (Ngn3) and dissociated adult islet cells (Islet) were used as negative and positive controls respectively. After pre-incubation with Krebs-Ringer buffer at 37° C. for 90 min, the cells were incubated at 37° C. for 60 min with basal D-glucose (2.75 mM) or stimulus D-glucose (27.5 mM). Then each conditioned medium was collected to determine the insulin concentration using an insulin ELISA kit. Data presented as mean±S.D., n=3. **: $P<0.01$ compared to uncultured purified Ngn3+ islet progenitors (Ngn3). (C) Expression of NeuroD, Ins2 and Ppy in matured insulin-secreting cells. qRT-PCR analysis of several genes expressed in matured insulin-secreting cells (β), compared to the negative control of uncultured, purified Ngn3+ progenitors (Ngn3) and positive control of adult functional islets (Islet).

To demonstrate conclusively that insulin-producing cells were derived from Ngn3⁺ progenitors, the inventors used a dual fluorescence reporter mouse line [Ngn3-GFP/RIP (rat insulin promoter)-DsRed]. Examination of the pancreas at selected stages demonstrated that expression of these reporters recapitulated expression of their tagged genes (FIG. 6a). Following dissection and dissociation, the GFP⁺DsRed⁻ (Ngn3⁺) progenitors were purified (~6.7% of viable cells, FIG. 6b) with a yield of 3,000-4,000 per fetal pancreas. Consistent with results in FIG. 2a, Ngn3-GFP⁺ progenitors were present in E-cad⁺ populations. Purified progenitors were confirmed to transiently express Ngn3 protein by immunofluorescence analysis (FIG. 6c), verifying the fidelity of the transgene. qPCR analysis also confirmed other islet progenitor genes including Insm1, Isl1, Myt1 and NeuroD were expressed in Ngn3⁺ progenitors (FIG. 6d). Ngn3 is only expressed in the progenitors that are destined to give rise to all islet cells, but not to acinar or ductal cells, thus excluding the possibility that the Ngn3-GFP⁺ population included the latter cells. To visualize differentiation and proliferation of Ngn3⁺ progenitors and differentiating cells, time-lapse life imaging was performed. The inventors found that Ngn3-GFP expression was down regulated while concurrently RIP-DsRed was up-regulated from undetectable to bright red in only 10 hours (FIG. 6e). There were no cell divisions observed by the life imaging system during this time. Consistently, FACS analysis showed that the number of DsRed⁺ cells increased progressively from 0% at the start of culture to 35% of all cells at day 4 (FIG. 6f, 16). Finally, as the half life of GFP is approximately 26 hr, the Ngn3-GFP$^+$ cells would represent a heterogeneous collection of all GFP$^+$ cells at different stages of their differentiation towards the islet lineages. There is a lack of markers for different stages of islet differentiation, but the inventors reasoned that GFP$^{High}$ cells might best represent Ngn3$^+$ progenitors rather than the GFP$^{dim}$ and GFP$^{medium}$ subpopulations. Indeed, GFP$^{High}$ cells (FIG. 6b) responded best to Nic stimulation (FIG. 6g), strongly supporting our conclusion of β-cell differentiation from Ngn3$^+$ progenitors.

Although present in the intestine at E15.5, GFP$^+$ progenitors purified from this tissue failed to differentiate into DsRed$^+$ cells in the same culture conditions. The inability to generate β cells from intestinal Ngn3$^+$ progenitors is because the latter are not programmed to give rise to insulin-secreting cells. Collectively, the inventor's studies provided compelling evidence that insulin-producing cells could be induced effectively by Nic de novo from Ngn3$^+$ progenitors with their established system.

Transcriptional Suppression during Differentiation.

Figure 3:
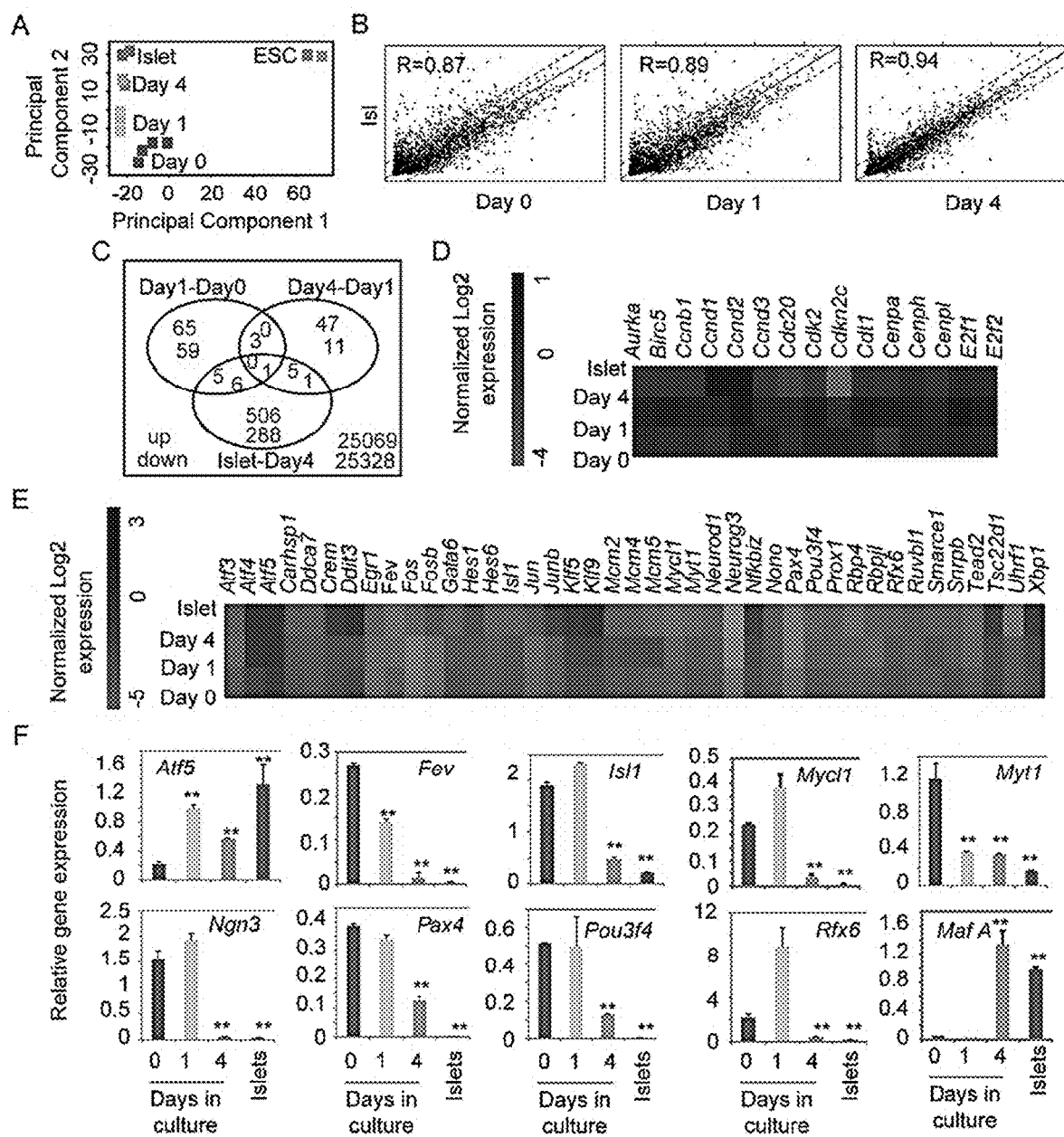
FIG. 3 Islet Progenitor Transcription Factor Genes Are Suppressed during Differentiation. (A) Principal component analysis of global gene profiles during differentiation of islet progenitors. (B) Pairewise cluster analysis of global gene profiles during differentiation of islet progenitors. (C) Venn diagram analysis of global gene profiles during differentiation of islet progenitors. (D) Heatmap analysis illustrating selective cell cycle genes during differentiation of islet progenitors. (E) Heatmap analysis showing islet progenitor transcription factor genes during differentiation of islet progenitors. (F) Real time RT-PCR analyses of islet progenitor transcription factor genes at indicated time points during differentiation. Data presented as mean±S.D., n=3. **: p<0.01.

In order to understand molecular mechanisms of differentiation, we performed transcriptome-wide gene expression analysis on cell fractions representing freshly sorted Ngn3-GFP$^+$ cells (day 0), as well as this same population that had been cultured for a further 1 or 4 days. Parallel analyses were performed on undifferentiated ESCs and adult islets for comparative purposes. Principal component analysis demonstrated that the global gene expression pattern of differentiating cells progressively clustered towards that observed for adult islets (FIG. 3A). Pairwise clustering analysis indicated that the cultured cells differentiated robustly towards the state of the adult islets (FIG. 3B). Representation of gene profiling data in the form of Venn diagrams illustrated that a few genes were continuously up- or down-regulated from one differentiation stage to another (FIG. 3C). This profiling also demonstrated that genes associated with cell cycle progression (e.g. Aurka, Birc5, Ccnb1, Ccnd3, Cdc20, Cdkn2a, Cenpa, Cenpl and E2f2) and genes that encode transcription factors regulating proliferation such as Egr1, Fos, Jun and Junb were progressively suppressed as cells differentiated between day 0 and day 4 (FIGS. 3D and 3E). These data supported our observation that Ngn3-GFP$^+$ progenitors did not divide when they gave rise to DsRed$^+$ cells (FIG. 16).

Importantly, key transcription regulator genes in islet progenitors included Fev, Hes6, Isl1, Mycl, Myt1, Ngn3, Pax4 and Rfx6 were also dramatically suppressed during differentiation (FIG. 3E). By analysis of a publically available microarray dataset we consistently found that approximately ⅔ of 130 transcription regulator genes including the above-described progenitor-associated transcription factor genes were suppressed when islet progenitors developed into adult endocrine cells. Supporting these gene profiling analyses, qRT-PCR assay confirmed the dramatic suppression of a subset of those genes, with down regulation between 3- and 26-fold over the course of culture (FIG. 3F). Conversely, we demonstrated up-regulation of Atf5, involved in terminal differentiation, and MafA (19-fold), a key transcription factor in functional β cells.

Characterization of Differentiated Insulin-producing Cells

Figure 4:
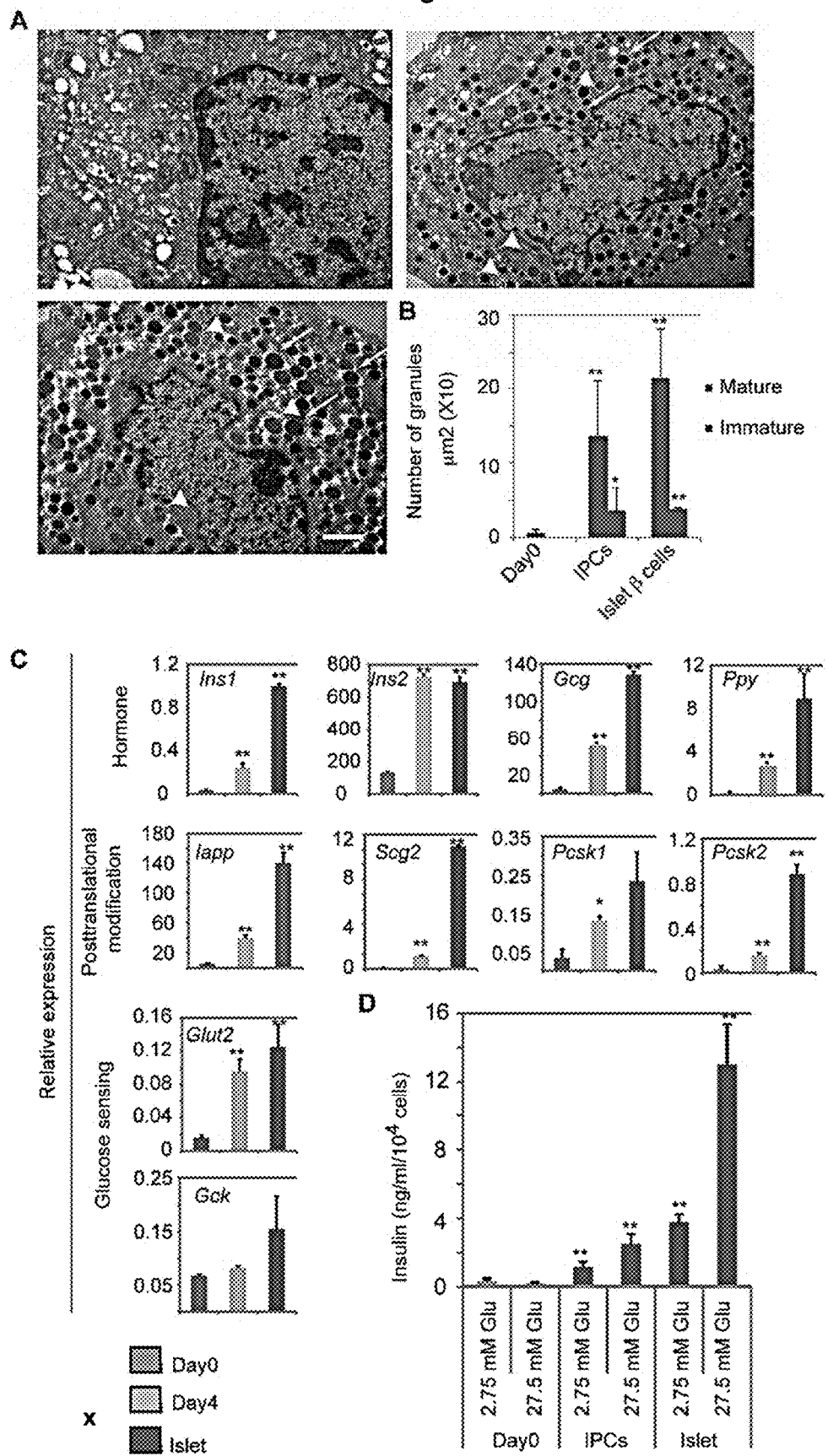
FIG. 4 In vitro Analysis of Differentiated Insulin-producing Cells. (A) Transmission electron microscopic analyses. Day0: namely uncultured Ngn3+ progenitor, IPC: differentiated β-like cell at day 4 of culture and Islet β cell: adult functional β cell, containing mature (arrowed) and immature (arrowheaded) insulin granules. Scale bar=1 μm. (B) Quantification of insulin secretion granules. (C) qRT-PCR analysis of selected genes in populations of differentiated cells. The expression levels of differentiation day 4 cells (Day4) and positive control of adult functional islets (Islet) were compared to the negative control of uncultured, purified Ngn3+ progenitors (Day0). (D) Glucose stimulated insulin secretion analysis. Differentiated cells were stimulated with basal glucose (2.75 mM) and stimulus glucose (27.5 mM). Supernatant was collected for determination of insulin concentration. Subsequently, culture was trypsinized and the number of DsRed+ IPCs determined. Data in (B-D) presented as mean±S.D., n=3. *: P<0.05, **: P<0.01 uncultured purified Ngn3+ progenitors (Day0).

Functional islet β cells make and store a large number of insulin secretory granules that can be observed under a transmission electron microscope due to their high electron densities. Transmission electron microscopy showed that insulin secretory granules were essentially absent from the pre-cultured islet progenitors (FIG. 4A). However, after as little as 4 days in culture, the differentiated IPCs contained equivalent numbers of both dense-core mature (arrowed) and pale immature insulin granules (arrow headed) as adult β cells (FIG. 4B).

Figure 7:
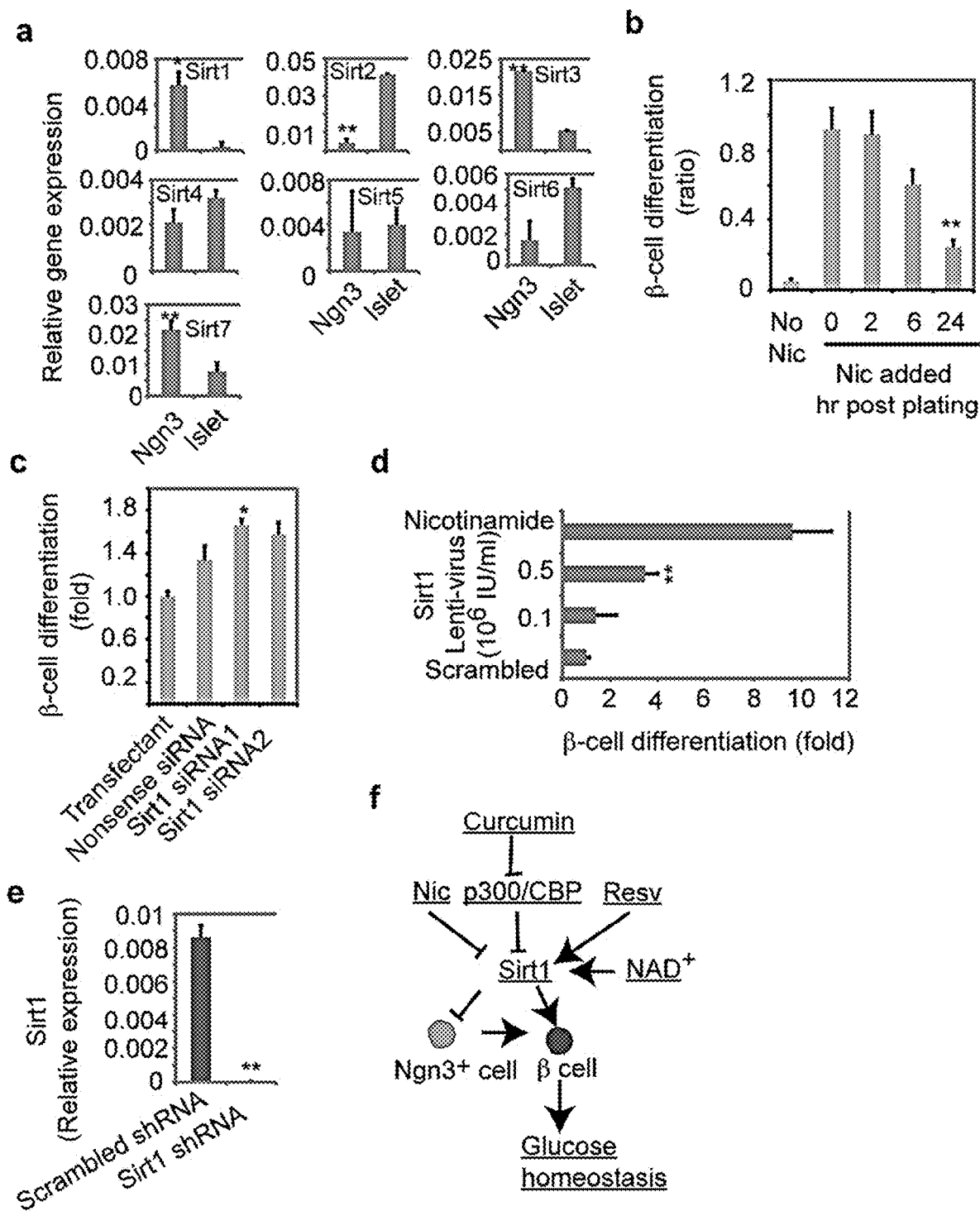
FIG. 7. Confirmation that Sirt1 negatively regulates insulin-producing cell differentiation. (a) Quantitative real time RT-PCR analysis of sirtuin transcript expression in purified GFP+DsRed− progenitors (Ngn3), compared to isolated adult functional islets (Islet). (b) Time-course of nicotinamide on insulin-producing cell differentiation. Purified Ngn3+ cells were plated and Nic was added at indicated times. The number of DsRed+ cells was determined at day 4. Data presented as mean±S.D., n=3. **: P<0.01 compared to 0 hr. (c) Sirt1 siRNA on insulin-producing cell differentiation. Purified GFP+DsRed− cells were plated and two types of siRNA to Sirt1 were transfected 2-3 hr after plating respectively. The number of DsRed+ cells was determined at day 4. Data presented as mean±S.D., n=3. *: P<0.05 compared to that with nonsense siRNA transfection. (d) Sirt1 shRNA lentivirus on insulin-producing cell differentiation. Sirt1 shRNA lentiviral and scrambled lentiviral particles on the number of DsRed+ cells were determined at day 4. Data presented as mean±S.D., n=3. **: P<0.01 compared to that with scrambled shRNA transfection. (e) Quantitative real time RT-PCR analysis of Sirt1 expression. Performed 2 days after transfection with Sirt1 shRNA lentiviral and scrambled lentiviral particles. (f) Schematic of the mechanisms underlying the differentiation of insulin-producing cells.

Confirmation that Sirt1 Negatively Regulates Insulin-Producing Cell Differentiation To demonstrate a direct effect of Sirt1, the inventors first confirmed expression of Sirt1 along with other sirtuins in purified Ngn3$^+$ progenitors. Unlike Sirt2 transcript, which was up-regulated approximately 10-fold, Sirt1, Sirt3 and Sirt7 genes were down-regulated 19-, 4- and 2.8-fold respectively when Ngn3$^+$ progenitors gave rise to adult islets whereas Sirt4-6 transcripts were low and unchanged (FIG. 7a). To examine when and whether knockdown of Sirt1 in Ngn3$^+$ progenitors could promote insulin-producing cell differentiation, the inventors determined the time-course of Nic on differentiation. The number of differentiated DsRed$^+$ cells was progressively reduced to approximately 40% of optimal levels when Nic was added at 24 hr (FIG. 7b). Therefore, the inventors selected 2-3 hr after plating to transfect Sirt1 siRNA and Sirt1 shRNA lentivirus to GFP$^+$ DsR$^-$ (Ngn3$^+$) progenitors in the absence of Nic. At day 4, the number of differentiated DsRed$^+$ cells significantly increased by approximately 30% and 400%, respectively, compared to controls (scrambled siRNA or shRNA) (FIG. 7c,d). Quantitative real time RT-PCR confirmed that Sirt1 was suppressed over 150-fold by the Sirt1 shRNA lentivirus compared to scrambled shRNA two days after transfection (FIG. 7e,f). Expression of the other sirtuin genes was unaffected or undetected (data not shown). Therefore, these results provided compelling evidence that Sirt1 negatively regulated insulin-producing cell differentiation.

Characterization of the Differentiated DsRed+ Cells.

Figure 8:
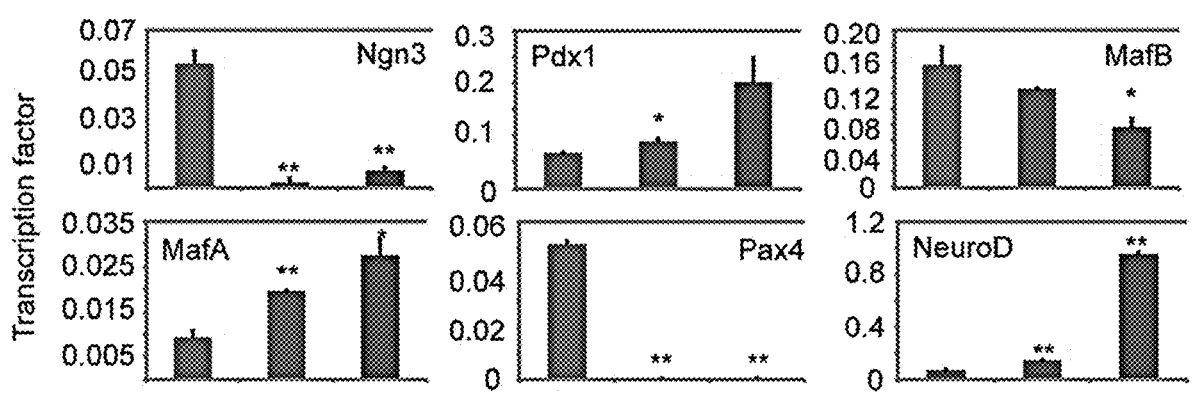
FIG. 8 The differentiated β-like cells are functional. (a) Expression of several categories of genes in differentiated β-like cells. Quantitative real time RT-PCR analysis of a suite of genes expressed in differentiated β-like cells (β-like), compared to the negative control of uncultured, purified Ngn3+ cells (Ngn3) and positive control of adult functional islets (Islet).

First, RT-qPCR analysis of a number of genes [including Ngn3, Pax4 (paired homeobox 4), Pdx1, MafB (v-maf oncogene homolog B), MafA and NeuroD] was undertaken and compared to levels in adult islets. In the differentiated DsRed$^+$ cells Ngn3, Pax4 and MafB were down-regulated to or near to adult levels, while Pdx1 and NeuroD were up-regulated to, and only approximately 15% of, the adult, respectively (FIG. 8).

To further characterize the differentiated cells, we performed qRT-PCR analysis of a selected cohort of genes that encode islet hormones, insulin-processing and -secreting products and glucose sensing systems. Critically, genes encoding Ins2 and glucose sensors (Glut2 also known as Slc2a2, and Gck) were up-regulated to, or near to, levels seen in adult islets (FIG. 4C). However, genes encoding proteins involved in insulin processing and secretion, and other hormonal genes, e.g. Iapp, Scg2, Pcsk1 and Pcsk2, and Ins1, Gcg and Ppy were only up-regulated to between 20% and 50% of adult levels (FIG. 4C). These data may indicate that the differentiated cells have not yet completely reached the adult islet state To examine their functional state, we tested the glucose responsiveness of the differentiated IPCs. As expected, uncultured Ngn3-GFP$^+$ islet progenitors did not significantly increase their secretion of insulin after stimulation with 27.5 mM glucose (FIG. 4D). In contrast, the differentiated DsRed$^+$ cells increased insulin secretion over 3- and 10-fold in response to basal 2.75 mM and stimulus 27.5 mM glucose, respectively (FIG. 4D). Taken together, these data demonstrated that the differentiated IPCs were functionally similar to β cells in adult islets.

Taken together, these data demonstrated that the differentiated cells might not be fully functional like those in adult islets; hence the inventors herein conservatively designate them as "β-like" cells.

In vivo Testing of the Differentiated β-like Cells.

Figure 9:
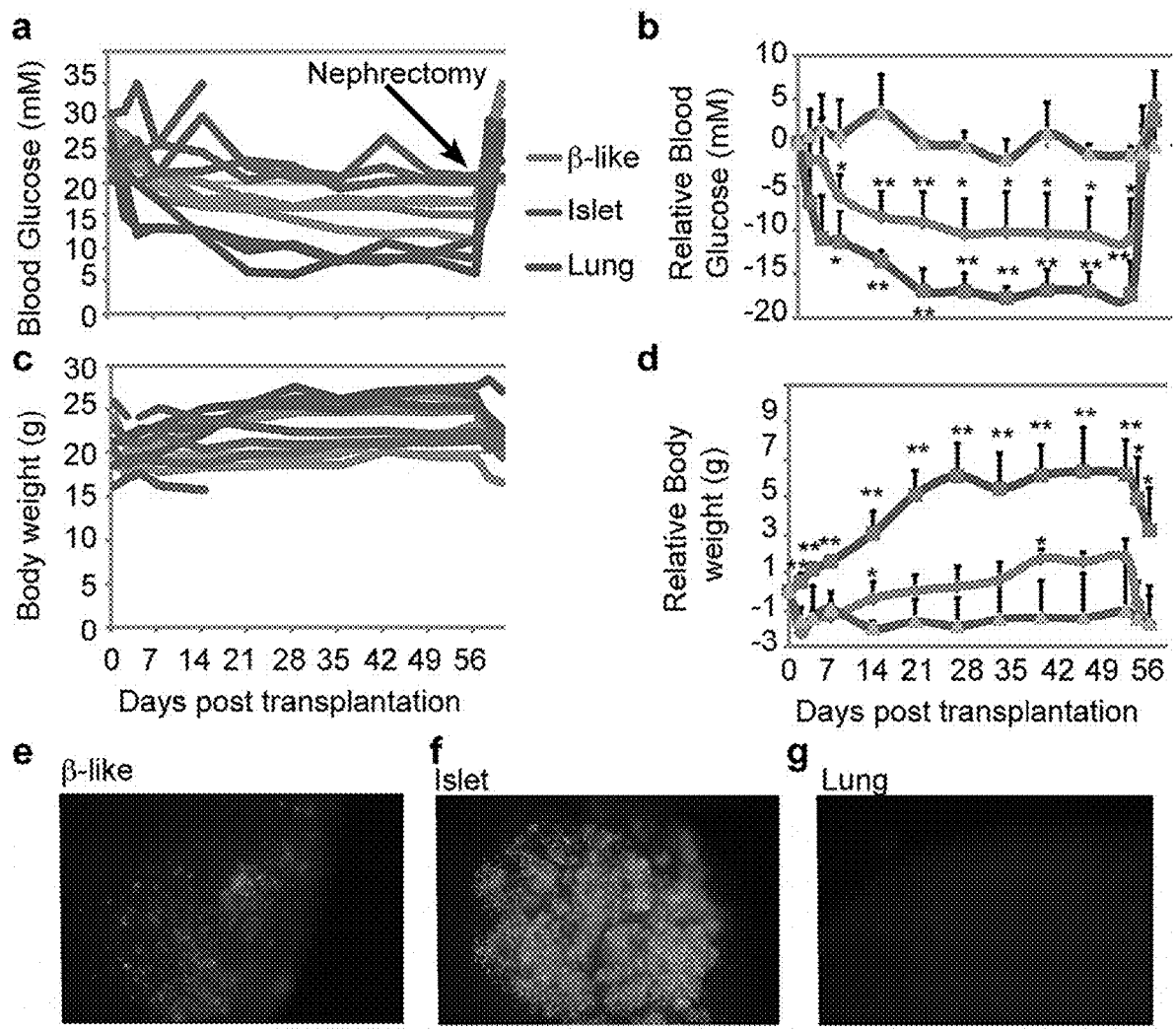
FIG. 9. Transplantation of differentiated β-like cells capable of reversing diabetes in recipient mice. (a-d) Differentiated β-like cells (β-like, n=4), isolated adult islets (Islet, positive control) and E15.5 lung cells (Lung, negative control) were transplanted under the kidney capsule of streptozotocin-induced diabetic SCID mice. (a-b) Blood glucose concentrations from individual mouse and relative group averages, respectively. (c-d) Body weight changes from individual mouse and relative group averages, respectively. *, p≤0.05; **, p≤0.01 compared to the negative control. (e-g) Whole mount DsRed images in grafted kidneys.

SCID mice were rendered diabetic by streptozotocin treatment. The differentiated β-like cells were transplanted under the kidney capsule of these mice. The grafted β-like cells were capable of progressively lowering, and in some instances normalizing, blood glucose concentrations (FIG. 9a,b). In all cases, body weight improved, similar to recipients of transplanted adult islets (FIG. 9c-d). Initially, we chose diabetic mice randomly to serve as recipients of experimental or control grafts. Control mice were transplanted with lung cells which, predictably, failed to lower blood glucose levels (FIG. 9a,b) and one mouse had to be sacrificed shortly after transplantation. To ensure longer survival, milder diabetic recipients were selected as the negative control in subsequent experiments. To confirm the function of transplanted cells, unilateral nephrectomy in the grafted side was performed at the end of experiments. Unlike in the negative control, blood glucose concentrations returned to or overtook the prior transplantation level within 4 days in both the experimental and positive control mice (FIG. 9a,b). Additionally, we observed strong red fluorescence (indicative of β cells) in whole mount samples of both experimental and positive control grafted kidneys, but not of the negative control (FIG. 9e-g). In conclusion, these data indicate that the mouse β-like cells differentiated from purified Ngn3+ progenitors carried out a similar function in ameliorating blood glucose levels in diabetic mice, as did adult islets.

Enriched Human Islet Progenitors Giving Rise to Insulin-Producing Cells

Figure 10C:
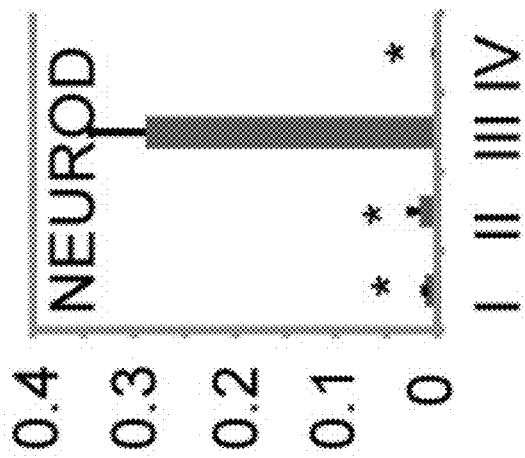
FIG. 10. Enriched human islet progenitors gave rise to insulin-producing cells. (a) Representative FACS profile to enrich human islet progenitors. The dissociated cells from a 19 week-old fetal pancreas were processed for sorting by FACS into populations as indicated. (b-d) Real time quantitative RT-PCR analysis of NGN3 (b), IA1 (c) and NEUROD (d). (e) Quantification of α and β cells in all cultured populations. The number of α and β cells in five populations after immunofluorescence staining was determined with the Image Pro Plus software installed in the computer. Five to 10 thousand cells per population were analyzed. Data in (b-e) presented as mean±SD, n=3, *: p<0.05. (f) Representative microphotographs from differentiated population III cells after immunofluorescence staining. The differentiated cells were fixed and stained with anti-human insulin (green) and anti-human glucagon (red) and with 4′,6-diamidino-2-phenylindole to counterstain DNA (blue).
Figure 10C:
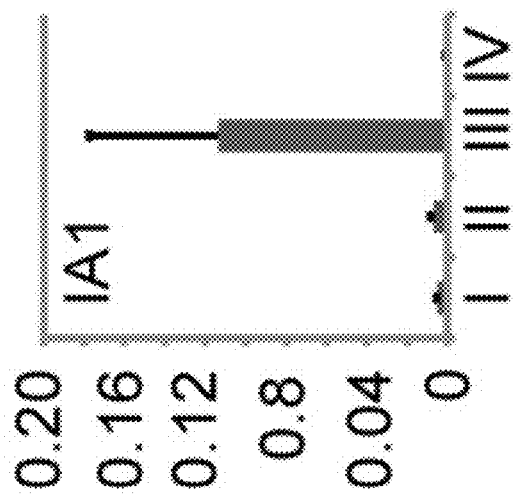
Figure 10A:
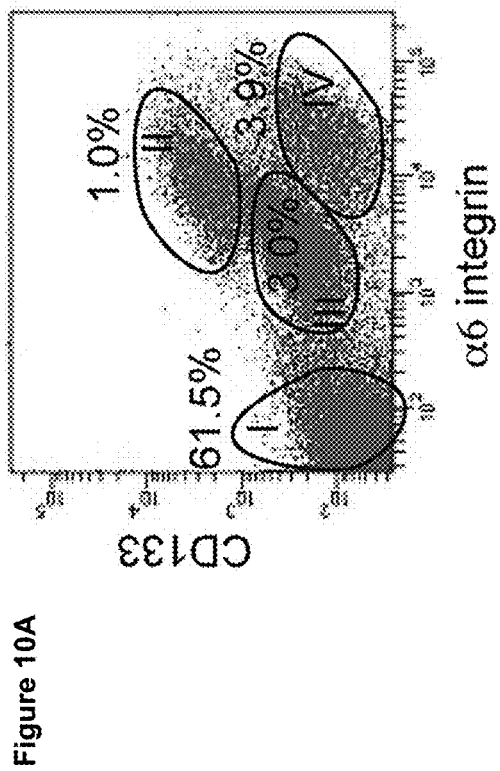
Figure 10B:
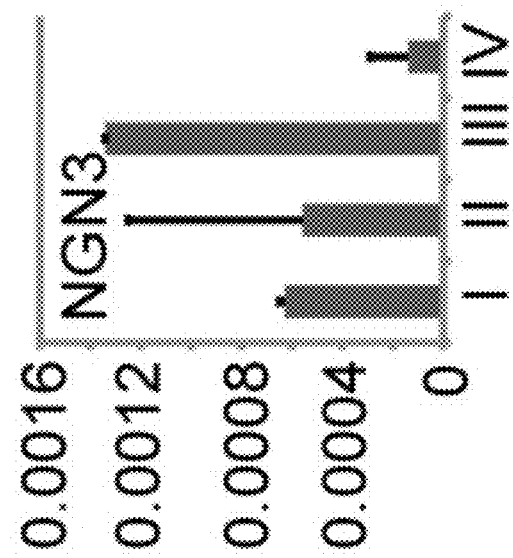

Finally, we determined whether the differentiation method established for mouse Ngn3+ progenitors was applicable for human islet progenitors. Following previously established protocol, the dissociated human pancreatic cells were FACS-separated into I-IV populations (FIG. 10a). The islet progenitors were enriched in population Ill marked by exclusive expression of high levels of NGN3, IA1 and NEUROD (FIG. 10b-d) detected by qRT-PCR analyses.

Figure 10E:
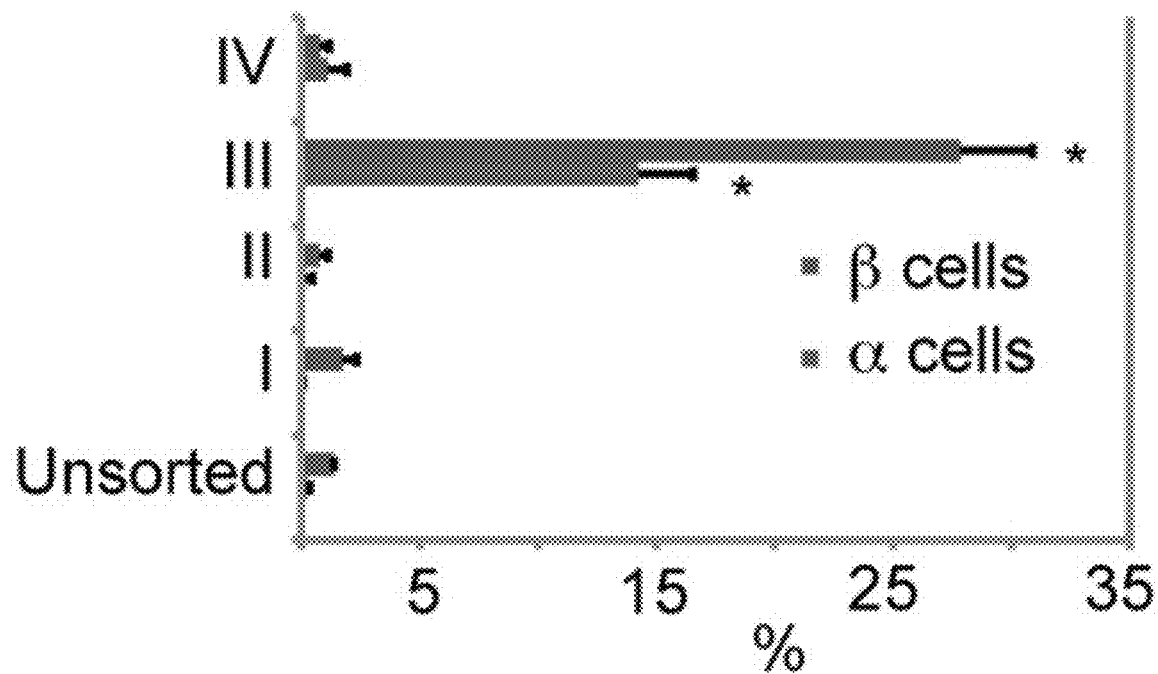
Figure 10F:
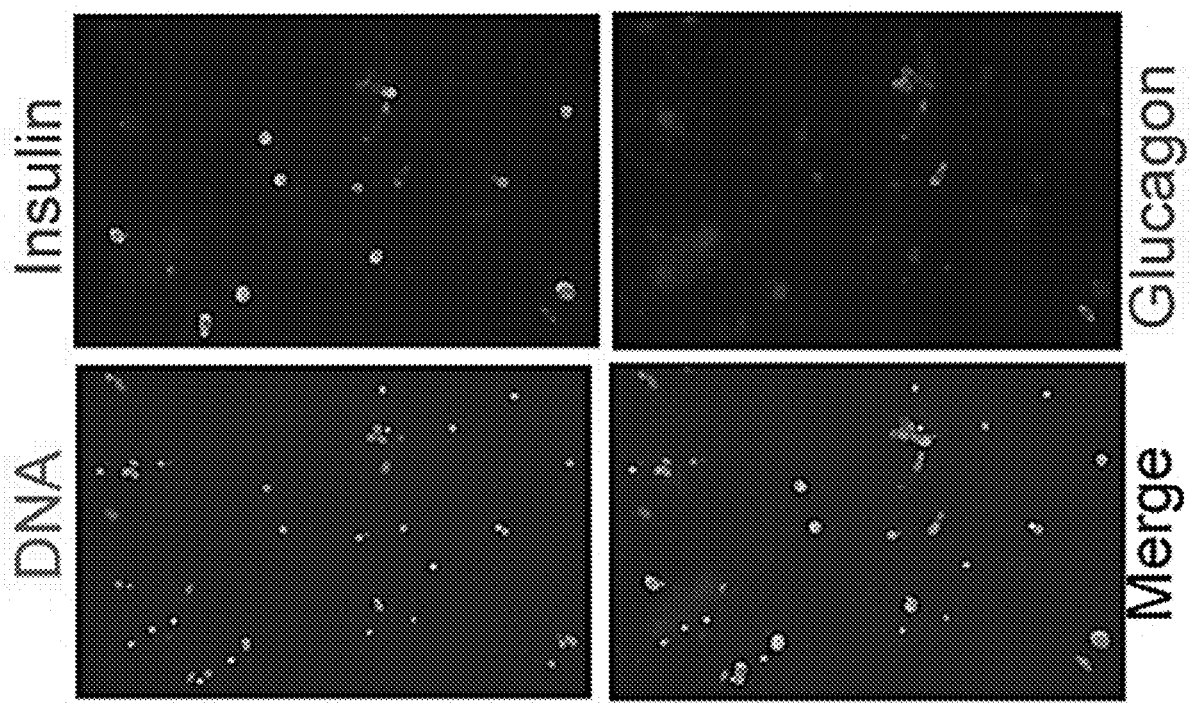

Four separated populations were cultured for 6 days in the presence of 10 mM Nic. In the cultured population III we detected immunochemically numerous single hormone-positive α and β cells unlike in remaining populations (FIG. 10e-f).

The original mouse β-cell line MIN6 cells share many features of adult islets. When continuously passaged in a high glucose condition (equivalent to hyperglycemia in diabetes), MIN6 cells gradually lose the glucose stimulated insulin secretion (GSIS) and underwent uncharacterised dedifferentiation. Surprisingly, the β-cell failure in type 2 diabetes was recently demonstrated to be caused by β-cell dedifferentiation into an islet progenitor-like state.

Figure 20:
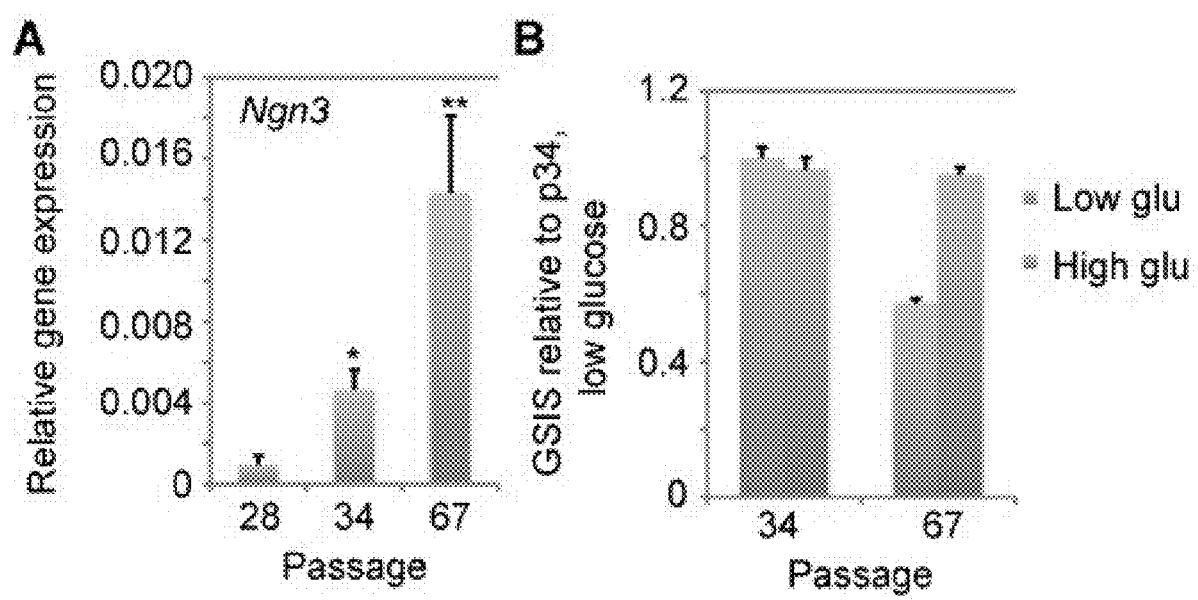
FIG. 20. Islet progenitor-like cells de-differentiated from highly passaged MIN6 cells were redifferentiated partially by Nic. (A) qRT-PCR analysis of Ngn3 expression. MIN6 cells were cultured and passaged as described previously. RNA was extracted from different passaged cells as indicated. (B) GSIS was performed as FIG. 8. Data presented as mean±S.D., n=3. *: $p<0.05$ and **: $P<0.01$ compared to lower passaged cells.
Figure 21:
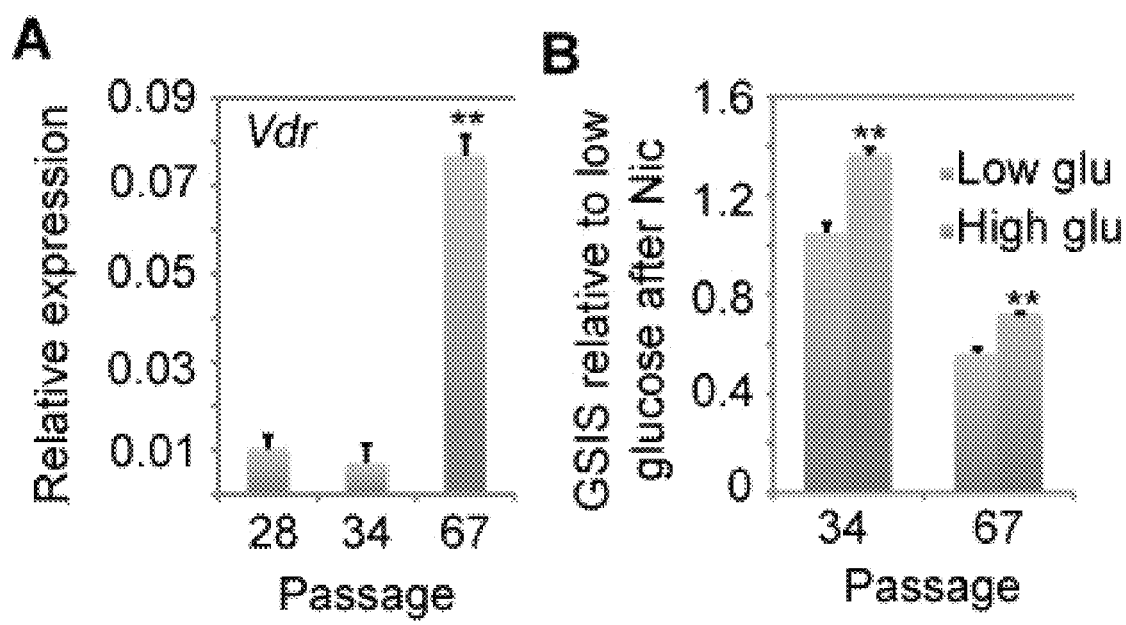
FIG. 21. Calcitriol primes dedifferentiated β cells from passaged MIN6 cells to regain partially glucose stimulated insulin secretion. (A) qRT-PCR analysis of Vdr expression. MIN6 cells were cultured and passaged as routinely. RNA was extracted from different passaged cells as indicated. (B) Calcitriol partially restores GSIS in heavily passaged MIN6 cells. MIN6 cells were cultured and passaged as routinely. GSIS was performed as FIG. 8. Data presented as mean±S.D., n=3. *: $p<0.05$ and **: $P<0.01$ compared to 2.75 mM glucose.

We here demonstrated that highly passaged MING cells dedifferentiate to islet progenitor-like cells characterised by up-regulation of Ngn3 and redifferentiated in the presence of Nic to regain partial GSIS, suggesting that the strategies we used for directed differentiation of islet progenitors may apply to directly redifferentiate islet progenitor-like cells in β-cell failure of type 2 diabetes (FIG. 20).

Methods

Enrichment/Purification of Islet Progenitors with Fluorescence Activated Cell Sorter (FACS)

Approximately 7,500 E15.5 [at which the number of Ngn3+ progenitors is peaked] mouse fetuses from both MIPGFP and Ngn3-GPF/RIP-DsRed lines were used for enrichment/purification of Ngn3+ progenitors. Mouse pancreases were dissected under a stereoscope (Olympus, Tokyo, Japan). Eleven human fetal pancreases were collected from 18-22 week-fetuses (Table 1) and minced. Both mouse and human pancreases were enzymatically dissociated into single cells under aseptic conditions. Rat anti-E-cadherin (E-cad, also known as CD324 or uvomorulin) monoclonal antibody IgG2a (Invitrogen, Carlsbad), Alexa Fluor 647 anti-E-cad (eBioscience), rat anti-integrin $\alpha_6$ subunit ($\alpha_6$, also known as CD49f) mAb IgG2a, phycoerythrin (PE) rat anti-human $\alpha_6$ (Becton Dickson Biosciences, San Jose), PE anti-mouse CD133 (also known as prominin I, eBioscience), biotin rabbit anti-rat immunoglobumins, allophycocyanin (APC) rat anti-mouse CD45 and APC rat anti-mouse TER119 and streptavidin APC-Cy7, streptavidin PE-Texas Red, streptavidin APC (BD Biosciences) or streptavidin Alexa Fluor 750 (Invitrogen), were used. After each incubation with antibodies, cells were washed twice with FACS buffer (0.1% bovine serum albumin in phosphate buffered saline) and finally re-suspended in this buffer containing 1 μg/ml propidium iodide (PI) or 4',6-diamidino-2-phenylindole (DAPI) for sorting (FACSAria II, Becton Dickson Labware, Bedford). The purity of sorted cells was determined by post-sort analysis. Data presented represented cell samples with over 90% purity.

TABLE 1

| Number | Age (weeks) | Sex | Cause of abortion |
|---|---|---|---|
| 1 | 20 | Female | Spinal bifida |
| 2 | 19 | Female | Neural tube defect |
| 3 | 20 | Female | Neural tube defect |
| 4 | 19 | Male | Neural tube defect |
| 5 | 20 | Male | Collagen defect |
| 6 | 20 | Female | Neural tube defect |
| 7 | 19 | Female | Neural tube defect |
| 8 | 20 | Male | Neural tube defect |
| 9 | 22 | Male | Neural tube defect |
| 10 | 19 | Female | Neural tube defect |
| 11 | 18 | Male | Neural tube defect |

Differentiation of Enriched/Purified Islet Progenitors

Sorted β-cell progenitor-enriched cells or Ngn3+ β-cell progenitors were differentiated in 96-, 12- or 6-well plates (BD Labware). The basal differentiation medium is Dulbecco's Modified Eagle Medium (Invitrogen) with 5.75 or 27.5 mM D-glucose supplemented with 1% B27 (Invitrogen) and 100 μg/ml streptomycin and 100 units/ml penicillin. Growth factor-reduced Matrigel (200 μg/ml, BD Biosciences) was overlayed onto cells in the presence of various potential regulators. Thyrotropin releasing hormone (TRH, 100 nM) was purchased from Auspep (Melbourne, Australia). Nicotinamide (pyridine-3-carboxylic acid amide, Nic, 10 mM), exendin-4 (Ex4, 50 ng/ml), N—[N-(3,5-difluorophenacetyl)-L-alanyl-sphenylglycinet-butylester (DAPT, 5 μM), quercetin (50 μM), isonicotinamide (INic, 10 mM), curcumin [(E, E)-1,7-bis (4-hydroxy-3-methoxyphenyl)-1,6-heptadiene-3,5-dione, 10 μM], resveratrol [5-[(1E)-2-(4-hydroxyphenyl) ethenyl]-1,3-benzenediol, 100 μM], sodium L-lactate (5 mM), sodium pyruvate, β-nicotinamide mononucleotide, sodium butyrate (2 mM) and trichostatin A were all purchased from Sigma (Sydney, Australia). (2'Z,3'E)-6-bromoindirubin-3'-oxime (B10, 5 μM) was bought from CalBiochem (Darmstadt, Germany). α-(1,3-dihydro-1,3-dioxo-2H-isoindo1-2-yl)-1H-indole-3-propanoic acid (RG-108, 10 μM) was obtained from Cayman Chemical (Ann Arbor). γ-secretase inhibitors X (1 μM) and inhibitor XXI (1 μM) and sinefungin (10 μM) were purchased from Merck (Melbourne, Australia). EX527 (6-chloro-2,3,4,9-tetrahydro-1H-carbazo-1-carboxamide, 10 μM) was from Tocris Bioscience (Bristol, UK). Cultures were incubated in 10% $CO_2$ 90% air at 37° C., for up to 8 days.

Normal glucose concentration is optimal for β-cell differentiation of Ngna$^+$ islet progenitors. The basal differentiation medium is Dulbecco's Modified Eagle Medium (Invitrogen) with 5.75, 11, 16.5 or 27.5 mM D-glucose supplemented with 2% B27 (Invitrogen) and 100 μg/ml streptomycin and 100 units/ml penicillin, overlayed with growth factor-reduced Matrigel (200 μg/ml, BD Biosciences). The differentiation medium contains the basal differentiation medium supplemented with 10 mM nicotinamide. Cultures were incubated in 10% CO2 90% air at 37° C., for 4 days.

Electron Microscopy

The purified GFP$^+$DsRed$^-$ (Ngn3$^+$) progenitors at days 0 and 4 of culture and adult islets were fixed in a glutaraldehyde-based fixative and processed for electron microscopy as described previously (Jiang, 1998). Insulin granules were categorized as described previously (Sato and Herman, 1981) and analyzed, and quantified with Nikon Element AR software (Version 4.13.01).

Real Time Life-Cell Imaging

The purified GFP$^+$DsRed$^-$ (Ngn3$^+$) progenitors were plated into Lab-Tek II Chambered Coverglasses (Thermo Fisher, Rochester), cultured overnight and then for life imaging loaded onto Eclipse Ti time-lapse life imaging system (Nikon, Tokyo, Japan) and analyzed with NIS-Elements AR Ver3.22 (64bit) software.

Quantification of Differentiated β-like Cells

The number of β-like cells was directly quantified under a fluorescence microscope. To verify the accuracy of cell count, at least five randomly chosen fields per well were microphotographed under the inverse IX71 Olympus fluorescence microscope (Olympus, Tokyo, Japan) and the number of β-like cells determined with the Image Pro Plus software installed in the computer.

Cell Culture

The β-cell line βTC3 cells were cultured in RPMI 1640 supplemented with 10% fetal calf serum, 100 μg/ml streptomycin, 100 units/ml penicillin and 2 mM glutamine (Invitrogen).

Sirt1 Knockdown

Two experimental (siRNA ID: s96764 and s96765, namely siRNA1 and siRNA2 respectively) siRNA to Sirt1 and one nonsense siRNA were purchased from Applied Biosystems (Melbourne) and transfected into GFP$^+$DsR$^-$ cells, approximately 2-3 hr after plating, with Dharma-FECT1 transfection reagent (Thermo Fisher Scientific, Melbourne, Australia) as per manufacturer's instruction. Sirt1 shRNA lentiviral and scrambled lentiviral particles were purchased from Santa Cruz and used to infect Ngn3$^+$ progenitors accordingly.

Indirect Immunofluorescence

Biotinylated anti-human insulin, rabbit anti-glucagon, rabbit anti Ngn3 polyclonal (1:1,000) and mouse anti-mouse Ngn3 monoclonal antibody (1:1,000) were from R&D Systems, Thermo Scientific, Millipore (Melbourne, Australia) and Developmental Studies Hybridoma Bank (Iowa City), respectively. Purified progenitors were cytospun onto slides and fixed in 4% paraformaldehyde. After staining with primary antibodies, cells were reacted with streptavidin FITC (BD) and Texas Red anti-rabbit or mouse (Vector Lab, Burlingame). In some cases, horseradish peroxidase-conjugated horse anti-mouse immunoglobulins (Cell Signaling, Beverly) and a tyramide signal amplification kit (Perkin-Elmer, Melbourne, Australia) were used following manufacturer's instruction. Slides were observed and microphotographed under the inverse IX71 Olympus fluorescence microscope (Olympus, Tokyo, Japan).

Gene Expression Analyses by Semi-Quantitative and Real Time Quantitative RT-PCR

Total RNA was extracted from enriched/purified, cultured and differentiated cells, E13.5 brain and E15.5 heart, liver and pancreas, E17.5 kidney and βTC3 cells with RNeasy Plus Mini Kit (Qiagen Science, Melbourne, Australia) or the Trizol-based method and quantified by a Nanodrop ND-1000 Spectrophotometer (Australian Biolabgroup, Melbourne, Australia). RNA (200-400 ng) was reverse transcribed with or without reverse transcriptase to cDNA in 40 μl, one μl of which (5-10 ng RNA/reaction) was amplified by PCR. Primer sequences are listed (Table 2).

Real time quantitative RT-PCR analysis was carried out using power SYBR Green PCR Master Mix and SYBR® Green Cells-to-Ct™ Kits purchased from Applied Biosystems (Foster City, USA). cDNA was amplified by PCR: 95° C. for 10 min, followed by 40 cycles of 95° C. for 15 sec and 60° C. for 1 min. The number of cycles of threshold (Ct) was measured with an ABI Prism 7900HT Sequence Detection System (Applied Biosystems) or a Rotor-Gene RG-3000 (Corbet Research, Sydney, Australia). All quantifications (ΔCt) were normalized with the internal 18s rRNA level ($2^{-\Delta Ct}$).

TABLE 2

| Gene | Forward primer | Reverse primer | Annealing temp. | Product |
| --- | --- | --- | --- | --- |
| IA1 | gccacccgtctgagaataga SEQ ID NO: 1 | ggagtcacagcgagaagacc SEQ ID NO: 2 | 60° C. | 231 bp |
| Pdx1 | gcgctcacctccaccaccacctt SEQ ID NO: 3 | gcggggccgggagatgtatttg SEQ ID NO: 4 | 65° C. | 290 bp |
| Ngn3 | ggtgccagctccccatcctat SEQ ID NO: 5 | gcgggcagtaaagacgacgaacat SEQ ID NO: 6 | 60° C. | 503 bp |
| NeuroD | cttggccaagaactacatctgg SEQ ID NO: 7 | ggagtagggatgcaccgggaa SEQ ID NO: 8 | 60° C. | 228 bp |
| Isl1 | cccgggggccactatttg SEQ ID NO: 9 | cgggcacgcatcacgaa SEQ ID NO: 10 | 60° C. | 397 bp |
| Ins1 | tggccctgttggtgcacttcctac SEQ ID NO: 11 | ggtcccgggcttcctc SEQ ID NO: 12 | 60° C. | 222 bp |

TABLE 2-continued

| Gene | Forward primer | Reverse primer | Annealing temp. | Product |
|---|---|---|---|---|
| Ins2 | ccaccccacccaggcttttgt<br>SEQ ID NO: 13 | agaggggtaggctgggtagtggtg<br>SEQ ID NO: 14 | 60° C. | 304 bp |
| Sirt1 | agttccagccgtctctgtgt<br>SEQ ID NO: 15 | ctccacgaacagcttcacaa<br>SEQ ID NO: 16 | 60° C. | 198 bp |
| Sirt2 | tgagctcaaagacccttcgt<br>SEQ ID NO: 17 | ttttggggtagcctgttgtc<br>SEQ ID NO: 18 | 60° C. | 235 bp |
| Sirt3 | aggtggaggaagcagtgaga<br>SEQ ID NO: 19 | gcttggggttgtgaaagaaa<br>SEQ ID NO: 20 | 60° C. | 230 bp |
| Sirt4 | tccaaaggctggaaatgaac<br>SEQ ID NO: 21 | gcgacacagctactccatca<br>SEQ ID NO: 22 | 60° C. | 213 bp |
| Sirt5 | ccaccgacagattcaggttt<br>SEQ ID NO: 23 | ccgttagtgccctgctttag<br>SEQ ID NO: 24 | 60° C. | 161 bp |
| Sirt6 | gggaacttgaaggaaccaca<br>SEQ ID NO: 25 | agcctgggctatagcagtga<br>SEQ ID NO: 26 | 60° C. | 202 bp |
| Sirt7 | gactgagcgtactgcccttc<br>SEQ ID NO: 27 | gctggaccctaaacacagga<br>SEQ ID NO: 28 | 60° C. | 165 bp |
| Gcg | ccgccgtgcccaagatttt<br>SEQ ID NO: 29 | cctgcggccgagttcct<br>SEQ ID NO: 30 | 60° C. | 232 bp |
| Gck | aggccacaaacattccagag<br>SEQ ID NO: 31 | tgagtgttgaagctgccatc<br>SEQ ID NO: 32 | 60° C. | 181 bp |
| Glut2 | gtcccatttctgccacactt<br>SEQ ID NO: 33 | tgtaggaggaggaggagcaa<br>SEQ ID NO: 34 | 60° C. | 192 bp |
| Iapp | tgggctgtagttcctgaagc<br>SEQ ID NO: 35 | gcacttccgtttgtccatct<br>SEQ ID NO: 36 | 60° C. | 199 bp |
| MafA | atcatcactctgcccaccat<br>SEQ ID NO: 37 | agtcggatgacctcctcctt<br>SEQ ID NO: 38 | 60° C. | 208 bp |
| MafB | gacaggctttgcgtcctaag<br>SEQ ID NO: 39 | cgttagttgccaatgtgtgg<br>SEQ ID NO: 40 | 60° C. | 200 bp |
| Pax4 | aagccgaggcactggagaaagag<br>SEQ ID NO: 41 | gtacactgccgggggactgct<br>SEQ ID NO: 42 | 60° C. | 249 bp |
| Pcsk2 | agcagccaaaatgcctctta<br>SEQ ID NO: 43 | cttgcctcttggttgtgtca<br>SEQ ID NO: 44 | 60° C. | 202 bp |
| Pcsk1 | ttggctgaaagggaaagaga<br>SEQ ID NO: 45 | gcttcatgtgctctggttga<br>SEQ ID NO: 46 | 60° C. | 202 bp |
| Ppy | gtacccaggcgactatgcgacacc<br>SEQ ID NO: 47 | ccacgggctgaagacaagaga<br>SEQ ID NO: 48 | 60° C. | 253 bp |
| Scg2 | gaagagagtgcccagtccag<br>SEQ ID NO: 49 | ctgtctgtttggggtgtcct<br>SEQ ID NO: 50 | 60° C. | 187 bp |
| Ngn3-GFP | agaccaccatggtgagcaagggcga<br>SEQ ID NO: 51 | ctgcttcatgtggtcggggtagcg<br>SEQ ID NO: 52 | 53° C. | 250 bp |
| RIP-DsRed | ggtgttgttgtccaatgagcac<br>SEQ ID NO: 53 | actcaccctgaagttctcag<br>SEQ ID NO: 54 | 53° C. | 226 bp |
| NGN3 | ccctctactccccagtctcc<br>SEQ ID NO: 55 | ccttacccttagcacccaca<br>SEQ ID NO: 56 | 60° C. | 176 bp |
| hIA1 | acccatccgaaaacagacag<br>SEQ ID NO: 57 | gagagaagcggagacgacac<br>SEQ ID NO: 58 | 60° C. | 206 bp |
| NEUROD | gttctcaggacgaggagcac<br>SEQ ID NO: 59 | gtctcttgggcttttgatcg<br>SEQ ID NO: 60 | 60° C. | 168 bp |

Frozen, Stored and Thawed Differentiated β Cells

Differentiated cells were trypsinized, harvested and reconstituted with 90% fetal calf serum and 10% dimethylsulfoxide. The cells were slowly frozen at −80° C., stored in a liquid nitrogen tank and quickly thawed in a 37° C. water bath.

Isolation of Adult Islets

Islets of Langerhans were isolated from 8-12 weeks old Ngn3-GFP/RIP-DsRed mice. Briefly, the pancreas was injected via the bile duct with collagenase P solution (dissolved in Hanks' balanced salt solution containing 2 mM $Ca^{2+}$ and 20 mM HEPES). Islets were isolated by density gradient centrifugation, washed, hand-picked for RNA (see above), and prior to transplantation cultured overnight at 37° C. in 5% $CO_2$ in CMRL medium-1066 (Gibco products Invitrogen) supplemented with 100 units/ml penicillin, 100 μg/ml streptomycin, 2 mM glutamine, and 10% FCS.

Genome-Wide Gene Profiling

Total RNA was extracted from differentiated cells at days 0, 1 and 4 and islets along with embryonic stem cells with Trizol reagent (Invitrogen) according to the manufacturer's instructions. The quality and concentration of the total RNA were determined with the Agilent Bioanalyzer 2100 system (Eukaryote total RNA Nano, Agilent Technologies, Melbourne, Australia). Samples with RNA integrity number ≥8 were used for further experiments. Three independent samples were performed for each time-point. Each RNA sample was processed with the Illumina© TotalPrep RNA Amplification Kit to produce labeled cRNA. The cRNA from each sample was then hybridized to an Illumine MouseRef-8 v2.1 Expression BeadChip (Illumina, San Diego, USA). Raw image data were generated with the Illumine BeadScanner.

Accession Code

The raw expression datasets were stored at Gene Expression Omnibus (http://www.ncbi.nlm.nih.gov/geo) with an accession number of GSE51944.

Bioinformatics Analysis

Global profiling datasets were analyzed as described previously (Jiang et al., 2010; Sui et al., 2012). Briefly, after quality check, $log_2$ transformation of raw datasets and interchip normalization, the differential expression of genes ($p \leq 0.05$; $-1 \leq log_2 \leq 1$) from one stage to another was analyzed using the Limma package in the "R" environment (http://bioinf.whi.edu.au/limma).

Streptozotocin Treatment, Transplantation and Blood Glucose Concentration

The recipient SCID mice were made diabetic by a single intraperitoneal injection at 160-175 mg/kg of streptozotocin (Sigma-Aldrich). Approximately $3 \times 10^5$ differentiated $DsRed^+$ (experimental) or E15.5 lung (negative control) cells were suspended in 20-30 μl growth factor-reduced Matrigel (BD) on ice and transferred to 3-4 mm long and wide×1.5 mm thick Gelfoam discs that have been pre-wetted with culture medium. Islets (~400/mouse) were transplanted as the positive control. The Gelfoam discs were gelled in an incubator at 37° C. for 15 min and then grafted under general anaesthesia into the kidney capsules in the diabetic mice. Tail venous blood was collected weekly for 8 weeks and glucose concentrations were measured with a glucose meter (Roche Diagnostics, Mannheim, Germany).

Glucose-Stimulated Insulin Secretion and Insulin Assay

The differentiated cells were washed twice with warm PBS. After pre-incubation with Krebs-Ringer buffer at 37° C. for 90 min, the cells were incubated at 37° C. for 60 min with basal D-glucose (2.75 mM) or stimulus D-glucose (27.5 mM). Then each conditioned medium was collected to determine the insulin concentration using an insulin ELISA kit (Mercodia AB, Uppsala, Sweden).

Statistical Analysis

Most experiments were performed in triplicate and repeated at least three times. Data are expressed as mean±standard deviation. Differences between groups were analyzed by non-parametric, unpaired Mann-Whitney U Tests or analysis of variance.

Indirect Immunofluorescence

Mouse anti-mouse Ngn3 monoclonal antibody (1:1,000) was bought from the Developmental Studies Hybridoma Bank (Iowa City). Mouse anti-proinsulin C-peptide monoclonal antibody (1:200) was purchased from Chemicon (Temecula). Rabbit antisera to porcine glucagon (1:100) and human somatostatin (1:200) were purchased from Dako (Glostrup, Denmark). Purified $E-cad^+$ and $E-cad^-$ cells were cytospun onto slides and fixed in 4% paraformaldehyde. After staining with primary antibodies, cells were reacted with Texas Red anti-mouse or anti-rabbit immunoglobulins (Vector Lab, Burlingame). To visualize Ngn3, horseradish peroxidase-conjugated horse anti-mouse immunoglobulins (Cell Signaling, Beverly) and a tyramide signal amplification kit (Perkin-Elmer, Melbourne, Australia) were used following manufacturer's instruction. Slides were observed and microphotographed under the inverse IX71 Olympus fluorescence microscope (Olympus, Tokyo, Japan).

Calcitriol Treatment

Nic-containing differentiation medium was removed from the differentiated β-like cells. A warmed maturation medium was added to the differentiated cells. The maturation medium is Dulbecco's Modified Eagle Medium (Invitrogen) with 5.75 mM D-glucose without nicotinamide (10 mM), 2% B27 (Invitrogen) and 100 μg/ml streptomycin and 100 units/ml penicillin supplemented with calcitriol (10 nM). Cultures were incubated in 10% CO2 90% air at 37° C., for 4 days.

Analysis of Maturation Factors

Expression heatmap showing a list of 61 genes that encode molecules important for metabolism, insulin secretion or glucose sensing as potential β-cell maturation factors. The microarray raw datasets were available from a public domain and analysed as described recently. Quantitative real time RT-PCR analysis of five short-listed genes including the calcitriol nuclear receptor gene Vdr. RNAs were extracted from mouse embryonic stem cells (ESCs), purified $Ngn3^+$ progenitors (Ngn3) and adult islets (Islet), respectively. Gene expression levels were normalised to the internal ribosomal 18s RNA level MIN6 Culture MIN6 cells were routinely maintained in a published protocol which contains Dulbecco's modified Eagle's medium (DMEM) containing 25 mM glucose, supplemented with 10% fetal calf serum, 2 mM L-glutamine, 25 mM Hepes, and 285 μM 2-mercaptoethanol. MIN6 cells presented in this study were at passages 30-40 (low passage, LP) or passages 60-70 (high passage, HP). All assays used MIN6 grown to 70-80% confluence unless otherwise stated.

Discussion

The inventors have established a unique culture with which purified mouse and human islet progenitors can be differentiated effectively into insulin-producing β-like cells in vitro. From the testing of a dozen potential epigenetic regulators, the inventors discovered that only Nic, a cell-permeable inhibitor of Sirt1, was able to promote this differentiation process in their serum-free and feeder-free method. No insulin-producing cells were observed at day 0 in culture, excluding a role of replication of pre-existing β cells for the progressive increase of β-like cell number. This conclusion also is supported by a time-course FACS analysis. No cell divisions were detectable by the life imaging system during the differentiation process, excluding a role of replication of differentiating insulin-producing cells in the increased number of β cells. As mouse Ngn3$^+$ progenitors are unipotent, it is most likely that committed β progenitors gave rise to β-like cells. Compared to mouse Ngn3, human NGN3 was less well understood. Apparently, the role of Ngn3 and NGN3 in development of mouse and human islet lineages differs respectively, as knockout of the former resulted in devoid of all islet cells whereas homozygous mutated humans only developed diabetes at 8-year old. Nevertheless whether NEUROD plays a more critical role for human islet cell differentiation requires further studies. Importantly, the ability for, in addition to the purified mouse counterpart, enriched human islet progenitors to give rise to insulin-producing cells indicates that our culture system might be applicable to differentiation of fetal pancreas-derived islet progenitors in other species.

The inventors provide evidence that Sirt1 suppresses β-cell differentiation. This conclusion was supported by the opposite effects of Nic and Resv and verified by effective differentiation after knockdown of Sirt1 via shRNA. The specificity of shRNA was confirmed by a specific 150-fold suppression of Sirt1, but not other sirtuin genes quantified by a qPCR analysis.

The inventors have established a differentiation system in which FACS-purified islet progenitors robustly form functional IPCs in vitro. Examination of a range of potential signals that might regulate this process revealed that only Nic efficiently drove isolated progenitors towards the β cell lineage. Nic has been previously supplemented for β-cell differentiation from highly self-renewable embryonic stem cells (ESCs) and induced pluripotent stem cells (iPSCs). Nevertheless, Nic was provided at the last stage of differentiation without knowing the target of activity and it is questionable whether the produced "functional" β cells are equivalent of adult endocrine cells. Surprisingly these "functional" cells only expressed ⅓ of adult marker MAFA, faintly/weakly for the critical β-cell marker Pdx1, merely released 13% C-peptide of adult islets after stimulating with 27.5 mM glucose or still transcribed highly for the endoderm marker SOX17. Similarly, using a new non-Nic containing protocol, mouse ESC-derived Ngn3-GFP$^+$ cells were only differentiated into polyhormonal (90%) positive cells that are proven not to be functional properly by several studies employing diverse methods such as functional characterization, transplantation assays and/or transcriptomic profiling. Although Nic was previously shown to increase DNA and insulin content in organ cultures of fetal pancreas, it was completely unknown whether it acted on functional or immature islet (Insulin$^+$) cells or by recruiting endocrine progenitors into the β cell differentiation pathway. Collectively, these data show that the differentiation of purified islet progenitors would be crucial to address this controversial issue. Indeed, this study not only resolves this problem by showing that Ngn3$^+$ islet progenitors are the target of Nic's pro-differentiation activity but also analyzes in depth the differentiating and end products.

The IPCs generated in this unique system resemble adult β cells in both intracellular ultrastructure and function. Flow cytometry analyses showed that the proportion of IPCs after our differentiation cultures increased from zero to approximately 35% at day 4, higher than any other report. This process was monitored using live cell imaging, which showed that transcription of the insulin promoter, as judged by expression of DsRed fluorescence, increased rapidly, with DsRed bright cells highly visible within 10 hours. This result accords with previous findings using Ngn3-Timer cells where initial green fluorescence shifted from green to red within 6 hours of in vitro culture. Live cell imaging experiments suggested that this differentiation process did not involve cell divisions, but rather a 1 to 1 conversion of progenitors into IPCS.

After only 4 days of in vitro differentiation, Ins2 and Glut2 were up regulated to levels comparable with that of adult β cells. Electron microscopy showed that the IPCs had an equivalent number of insulin secretory granules to adult functional β cells. Consistent with this, The inventors found that, in contrast to Ngn3$^+$ islet progenitors, differentiated IPCs displayed a 3-10-fold increase in insulin secretion following glucose-stimulation. Last and most critically, grafted cells stabilized and controlled blood glucose levels in diabetic recipient mice without the requirement of exogenous insulin injection.

In this differentiation, Gcg and Ppy were also up-regulated, suggesting that there were glucagon- and PP-producing cells present in the differentiated products; a conclusion that could be systematically tested using appropriate reporter lines. Nevertheless, the presence of a cells in our enriched human islet progenitor cultures supports the idea that Nic promotes differentiation of non-β progenitors.

Mitosis was not observed during the live imaging of differentiating cells, consistent with previous lineage tracing and genetic clonal analyses that showed Ngn3$^+$ progenitors were non-proliferative. These early experiments used Ngn3-directed Cre transcription to drive recombination of LoxP sites flanking a stable sequence. However, because there may be up 2 hours delay between the transcription of Cre and its action on target locus, whether a Ngn3$^+$ cell can give rise to multiple or only to single islet cell remains to be resolved. In this context, the application of our system, together with a novel tracing strategies and single cell genomics might clarify the differentiation potential of pancreatic Ngn3$^+$ progenitors.

The inventors unique system provided an unprecedented opportunity to explore the molecular mechanisms by which how the differentiation of Ngn3$^+$ islet progenitors is regulated at the genome scale. Although remarkable progress has been made on many individual up- or down-stream regulators including Ngn3, Isl1, Pax4, Myt1 and Rfx6, how these regulators together orchestrate the decision-making process is completely unknown. The inventors genome-wide profiling revealed that a range of genes associated with proliferation was suppressed, explaining why Ngn3$^+$ progenitors were non-proliferative during differentiation. In the 4-day culture period, the global mRNA profiles of differentiating cells progressively clustered towards that of adult islets, corroborating our results of in vitro and in vivo functional studies.

The inventors transcriptomic profiling demonstrates that an array of key transcription regulators including Fey, Isl1, Mycl1, Myt1, Pax4, Pou3f4 and Rfx6 were dramatically suppressed when purified islet progenitors gave rise to IPCs in vitro. A similar suppression was also observed in the reanalysis of a publically available global gene profiling of purified islet progenitors and isolated adult islets. Ngn3 and Myt1 are shown to positively activate each other's expression during islet differentiation. Taken together, we propose that multiple transcription factor genes function collaboratively as negative regulators for the differentiation of islet progenitors. Understanding the underlying molecular mechanisms of how these genes are suppressed would further improve the direct differentiation of islet lineages The inventors have established an accelerated differentiation method in which purified β-cell progenitors give rise effectively to functional β-like cells, and for purified Ngn3+ progenitors to reduce hyperglycemia immediately after transplantation. First, insulin translation is undertaken robustly and rapidly, as indicated by progenitor cells progressing from invisible to bright red in as short as 10 hr with the life imaging system. Second, after only 4 days in culture, Ins2 was up-regulated approximately 40-fold and Iapp, Scg2 and GIut2 close to the adult level whereas Ngn3 and Pax6 were down-regulated to their adult islet levels. Third, in contrast to Ngn3+ progenitors that do not respond to glucose stimulus, differentiated 3-like cells increased 3-10-fold glucose-stimulated insulin secretion after 4 day-culture. Fourth, differentiated β-like cells immediately stabilized and ameliorated blood glucose levels in diabetic recipient mice without the requirement of exogenous insulin injections. Recipients' glucose levels were progressively lowered towards euglycemia. While blood glucose concentrations were not completely normalized within the experimental period, unlike those in positive control recipients transplanted with adult islets, there are several explanations for this. For example, the differentiated β-like cells had not yet developed fully a gene-expression program typical of mature islets. The up-regulated levels of hormonal genes were only similar to that of NeuroD, but not of most genes encoding transcription factors, insulin posttranslational modification or glucose sensing proteins, supporting a recent finding that NeuroD is required for β-cell maturation. Importantly, we have now identified a critical factor calcitriol and analogues thereof with which NeuroD is further up-regulated and β-like cells are fully matured. Due to the fact that the method of the invention works equally well in both humans and mice, this method is also expected to be effective for differentiation of the β-cell progenitors from other species.

The invention claimed is:

1. A method to generate mature insulin-producing β-like cells for treating a subject with diabetes mellitus, the method consisting essentially of the steps of:
    (a) exposing purified, and/or enriched β cell progenitor cells to a Sirt1 inhibitor at a concentration sufficient to cause differentiation of the β-cell progenitor cells into immature insulin-producing β-like cells;
    wherein the immature insulin producing β-like cells have insulin granule numbers equivalent to adult β cells, and secrete approximately 10-fold more insulin content in response to stimulation with basal glucose and stimulus glucose compared to islet progenitor cells; and
    (b) exposing the immature insulin-producing β-like cells to calcitriol or an analogue thereof in vitro at a concentration sufficient to cause maturation of the immature insulin-producing β-like cells;
    wherein the mature insulin-producing β-like cells secrete insulin content in response to basal glucose and stimulus glucose equivalent to healthy adult islets and at least 4-fold more compared to immature insulin-producing β-like cells.

2. The method according to claim 1, wherein said subject has Type 1 or 2 diabetes mellitus.

3. The method according to claim 1, wherein the subject is a human.

4. The method of claim 1, wherein the Sirt1 is inhibited by 10 mM nicotinamide.

5. The method of claim 1, wherein the Sirt1 is inhibited by a nicotinamide analogue, wherein said nicotinamide analogue causes differentiation of β-cell progenitor cells into immature insulin-producing β-like cells.

6. The method of claim 1, further comprising a step of analyzing the mature insulin-producing β-like cells in vitro to determine the levels of expression of insulin in response to exposure of the insulin-producing β-like cells to glucose.

7. The method of claim 1, wherein the population of β cell progenitor cells are exposed to the Sirt1 inhibitor between 4 and 8 days.

8. The method of claim 7, wherein the population of β cell progenitor cells are exposed to the Sirt1 inhibitor between 4 and 6 days.

* * * * *

SEQUENCE LISTING

```
<160> NUMBER OF SEQ ID NOS: 60

<210> SEQ ID NO 1
<211> LENGTH: 20
<212> TYPE: DNA
<213> ORGANISM: Mus musculus

<400> SEQUENCE: 1
gccacccgtc tgagaataga                                              20

<210> SEQ ID NO 2
<211> LENGTH: 20
<212> TYPE: DNA
<213> ORGANISM: Mus musculus

<400> SEQUENCE: 2
ggagtcacag cgagaagacc                                              20

<210> SEQ ID NO 3
<211> LENGTH: 23
<212> TYPE: DNA
<213> ORGANISM: Mus musculus

<400> SEQUENCE: 3
gcgctcacct ccaccaccac ctt                                          23

<210> SEQ ID NO 4
<211> LENGTH: 22
<212> TYPE: DNA
<213> ORGANISM: Mus musculus

<400> SEQUENCE: 4
gcggggccgg gagatgtatt tg                                           22

<210> SEQ ID NO 5
<211> LENGTH: 22
<212> TYPE: DNA
<213> ORGANISM: Mus musculus

<400> SEQUENCE: 5
ggtgcccagc tccccatcct at                                           22
```

-continued

```
<210> SEQ ID NO 6
<211> LENGTH: 24
<212> TYPE: DNA
<213> ORGANISM: Mus musculus

<400> SEQUENCE: 6
gcgggcagta aagacgacga acat                                          24

<210> SEQ ID NO 7
<211> LENGTH: 22
<212> TYPE: DNA
<213> ORGANISM: Mus musculus

<400> SEQUENCE: 7
cttggccaag aactacatct gg                                            22

<210> SEQ ID NO 8
<211> LENGTH: 21
<212> TYPE: DNA
<213> ORGANISM: Mus musculus

<400> SEQUENCE: 8
ggagtaggga tgcaccggga a                                             21

<210> SEQ ID NO 9
<211> LENGTH: 18
<212> TYPE: DNA
<213> ORGANISM: Mus musculus

<400> SEQUENCE: 9
cccgggggcc actatttg                                                 18

<210> SEQ ID NO 10
<211> LENGTH: 17
<212> TYPE: DNA
<213> ORGANISM: Mus musculus

<400> SEQUENCE: 10
cgggcacgca tcacgaa                                                  17

<210> SEQ ID NO 11
<211> LENGTH: 24
<212> TYPE: DNA
<213> ORGANISM: Mus musculus

<400> SEQUENCE: 11
tggccctgtt ggtgcacttc ctac                                          24

<210> SEQ ID NO 12
<211> LENGTH: 18
<212> TYPE: DNA
<213> ORGANISM: Mus musculus

<400> SEQUENCE: 12
ggtccccggg gcttcctc                                                 18

<210> SEQ ID NO 13
<211> LENGTH: 21
<212> TYPE: DNA
<213> ORGANISM: Mus musculus

<400> SEQUENCE: 13
ccaccccacc caggcttttg t                                             21
```

```
<210> SEQ ID NO 14
<211> LENGTH: 24
<212> TYPE: DNA
<213> ORGANISM: Mus musculus

<400> SEQUENCE: 14
agaggggtag gctgggtagt ggtg                                          24

<210> SEQ ID NO 15
<211> LENGTH: 20
<212> TYPE: DNA
<213> ORGANISM: Mus musculus

<400> SEQUENCE: 15
agttccagcc gtctctgtgt                                               20

<210> SEQ ID NO 16
<211> LENGTH: 20
<212> TYPE: DNA
<213> ORGANISM: Mus musculus

<400> SEQUENCE: 16
ctccacgaac agcttcacaa                                               20

<210> SEQ ID NO 17
<211> LENGTH: 20
<212> TYPE: DNA
<213> ORGANISM: Mus musculus

<400> SEQUENCE: 17
tgagctcaaa gacccttcgt                                               20

<210> SEQ ID NO 18
<211> LENGTH: 20
<212> TYPE: DNA
<213> ORGANISM: Mus musculus

<400> SEQUENCE: 18
ttttggggta gcctgttgtc                                               20

<210> SEQ ID NO 19
<211> LENGTH: 20
<212> TYPE: DNA
<213> ORGANISM: Mus musculus

<400> SEQUENCE: 19
aggtggagga agcagtgaga                                               20

<210> SEQ ID NO 20
<211> LENGTH: 20
<212> TYPE: DNA
<213> ORGANISM: Mus musculus

<400> SEQUENCE: 20
gcttggggtt gtgaaagaaa                                               20

<210> SEQ ID NO 21
<211> LENGTH: 20
<212> TYPE: DNA
<213> ORGANISM: Mus musculus

<400> SEQUENCE: 21
tccaaaggct ggaaatgaac                                               20
```

```
<210> SEQ ID NO 22
<211> LENGTH: 20
<212> TYPE: DNA
<213> ORGANISM: Mus musculus

<400> SEQUENCE: 22
gcgacacagc tactccatca                                                  20

<210> SEQ ID NO 23
<211> LENGTH: 20
<212> TYPE: DNA
<213> ORGANISM: Mus musculus

<400> SEQUENCE: 23
ccaccgacag attcaggttt                                                  20

<210> SEQ ID NO 24
<211> LENGTH: 20
<212> TYPE: DNA
<213> ORGANISM: Mus musculus

<400> SEQUENCE: 24
ccgttagtgc cctgctttag                                                  20

<210> SEQ ID NO 25
<211> LENGTH: 20
<212> TYPE: DNA
<213> ORGANISM: Mus musculus

<400> SEQUENCE: 25
gggaacttga aggaaccaca                                                  20

<210> SEQ ID NO 26
<211> LENGTH: 20
<212> TYPE: DNA
<213> ORGANISM: Mus musculus

<400> SEQUENCE: 26
agcctgggct atagcagtga                                                  20

<210> SEQ ID NO 27
<211> LENGTH: 20
<212> TYPE: DNA
<213> ORGANISM: Mus musculus

<400> SEQUENCE: 27
gactgagcgt actgcccttc                                                  20

<210> SEQ ID NO 28
<211> LENGTH: 20
<212> TYPE: DNA
<213> ORGANISM: Mus musculus

<400> SEQUENCE: 28
gctggaccct aaacacagga                                                  20

<210> SEQ ID NO 29
<211> LENGTH: 19
<212> TYPE: DNA
<213> ORGANISM: Mus musculus

<400> SEQUENCE: 29
```

```
ccgccgtgcc caagatttt                                                   19

<210> SEQ ID NO 30
<211> LENGTH: 17
<212> TYPE: DNA
<213> ORGANISM: Mus musculus

<400> SEQUENCE: 30
cctgcggccg agttcct                                                     17

<210> SEQ ID NO 31
<211> LENGTH: 20
<212> TYPE: DNA
<213> ORGANISM: Mus musculus

<400> SEQUENCE: 31
aggccacaaa cattccagag                                                  20

<210> SEQ ID NO 32
<211> LENGTH: 20
<212> TYPE: DNA
<213> ORGANISM: Mus musculus

<400> SEQUENCE: 32
tgagtgttga agctgccatc                                                  20

<210> SEQ ID NO 33
<211> LENGTH: 20
<212> TYPE: DNA
<213> ORGANISM: Mus musculus

<400> SEQUENCE: 33
gtcccatttc tgccacactt                                                  20

<210> SEQ ID NO 34
<211> LENGTH: 20
<212> TYPE: DNA
<213> ORGANISM: Mus musculus

<400> SEQUENCE: 34
tgtaggagga ggaggagcaa                                                  20

<210> SEQ ID NO 35
<211> LENGTH: 20
<212> TYPE: DNA
<213> ORGANISM: Mus musculus

<400> SEQUENCE: 35
tgggctgtag ttcctgaagc                                                  20

<210> SEQ ID NO 36
<211> LENGTH: 20
<212> TYPE: DNA
<213> ORGANISM: Mus musculus

<400> SEQUENCE: 36
gcacttccgt ttgtccatct                                                  20

<210> SEQ ID NO 37
<211> LENGTH: 20
<212> TYPE: DNA
<213> ORGANISM: Mus musculus

<400> SEQUENCE: 37
```
atcatcactc tgcccaccat                                                    20

<210> SEQ ID NO 38
<211> LENGTH: 20
<212> TYPE: DNA
<213> ORGANISM: Mus musculus

<400> SEQUENCE: 38
agtcggatga cctcctcctt                                                    20

<210> SEQ ID NO 39
<211> LENGTH: 20
<212> TYPE: DNA
<213> ORGANISM: Mus musculus

<400> SEQUENCE: 39
gacaggcttt gcgtcctaag                                                    20

<210> SEQ ID NO 40
<211> LENGTH: 20
<212> TYPE: DNA
<213> ORGANISM: Mus musculus

<400> SEQUENCE: 40
cgttagttgc caatgtgtgg                                                    20

<210> SEQ ID NO 41
<211> LENGTH: 23
<212> TYPE: DNA
<213> ORGANISM: Mus musculus

<400> SEQUENCE: 41
aagccgaggc actggagaaa gag                                                23

<210> SEQ ID NO 42
<211> LENGTH: 21
<212> TYPE: DNA
<213> ORGANISM: Mus musculus

<400> SEQUENCE: 42
gtacactgcc gggggactgc t                                                  21

<210> SEQ ID NO 43
<211> LENGTH: 20
<212> TYPE: DNA
<213> ORGANISM: Mus musculus

<400> SEQUENCE: 43
agcagccaaa atgcctctta                                                    20

<210> SEQ ID NO 44
<211> LENGTH: 20
<212> TYPE: DNA
<213> ORGANISM: Mus musculus

<400> SEQUENCE: 44
cttgcctctt ggttgtgtca                                                    20

<210> SEQ ID NO 45
<211> LENGTH: 20
<212> TYPE: DNA
<213> ORGANISM: Mus musculus
<210> SEQ ID NO 45
<211> LENGTH: 20
<212> TYPE: DNA
<213> ORGANISM: Mus musculus

<400> SEQUENCE: 45
ttggctgaaa gggaaagaga                                          20

<210> SEQ ID NO 46
<211> LENGTH: 20
<212> TYPE: DNA
<213> ORGANISM: Mus musculus

<400> SEQUENCE: 46
gcttcatgtg ctctggttga                                          20

<210> SEQ ID NO 47
<211> LENGTH: 24
<212> TYPE: DNA
<213> ORGANISM: Mus musculus

<400> SEQUENCE: 47
gtacccaggc gactatgcga cacc                                     24

<210> SEQ ID NO 48
<211> LENGTH: 21
<212> TYPE: DNA
<213> ORGANISM: Mus musculus

<400> SEQUENCE: 48
ccacgggctg aagacaagag a                                        21

<210> SEQ ID NO 49
<211> LENGTH: 20
<212> TYPE: DNA
<213> ORGANISM: Mus musculus

<400> SEQUENCE: 49
gaagagagtg cccagtccag                                          20

<210> SEQ ID NO 50
<211> LENGTH: 20
<212> TYPE: DNA
<213> ORGANISM: Mus musculus

<400> SEQUENCE: 50
ctgtctgttt ggggtgtcct                                          20

<210> SEQ ID NO 51
<211> LENGTH: 25
<212> TYPE: DNA
<213> ORGANISM: Mus musculus

<400> SEQUENCE: 51
ggaccaccat ggtgagcaag ggcga                                    25

<210> SEQ ID NO 52
<211> LENGTH: 24
<212> TYPE: DNA
<213> ORGANISM: Mus musculus

<400> SEQUENCE: 52
ctgcttcatg tggtcggggt agcg                                     24

<210> SEQ ID NO 53
<211> LENGTH: 22
<212> TYPE: DNA
<213> ORGANISM: Mus musculus

```
<400> SEQUENCE: 53
ggtgttgttg tccaatgagc ac                                              22

<210> SEQ ID NO 54
<211> LENGTH: 20
<212> TYPE: DNA
<213> ORGANISM: Mus musculus

<400> SEQUENCE: 54
actcaccctg aagttctcag                                                 20

<210> SEQ ID NO 55
<211> LENGTH: 20
<212> TYPE: DNA
<213> ORGANISM: Mus musculus

<400> SEQUENCE: 55
ccctctactc cccagtctcc                                                 20

<210> SEQ ID NO 56
<211> LENGTH: 20
<212> TYPE: DNA
<213> ORGANISM: Mus musculus

<400> SEQUENCE: 56
ccttaccctt agcacccaca                                                 20

<210> SEQ ID NO 57
<211> LENGTH: 20
<212> TYPE: DNA
<213> ORGANISM: Mus musculus

<400> SEQUENCE: 57
acccatccga aaacagacag                                                 20

<210> SEQ ID NO 58
<211> LENGTH: 20
<212> TYPE: DNA
<213> ORGANISM: Mus musculus

<400> SEQUENCE: 58
gagagaagcg gagacgacac                                                 20

<210> SEQ ID NO 59
<211> LENGTH: 20
<212> TYPE: DNA
<213> ORGANISM: Mus musculus

<400> SEQUENCE: 59
gttctcagga cgaggagcac                                                 20

<210> SEQ ID NO 60
<211> LENGTH: 20
<212> TYPE: DNA
<213> ORGANISM: Mus musculus

<400> SEQUENCE: 60
gtctcttggg cttttgatcg                                                 20
```